(12) United States Patent
Kim et al.

(10) Patent No.: US 12,343,335 B2
(45) Date of Patent: Jul. 1, 2025

(54) PHARMACEUTICAL COMPOSITION FOR TREATING MULTIPLE SCLEROSIS ON BASIS OF AMPK INHIBITORY FUNCTION AND ZINC HOMEOSTASIS CONTROL FUNCTION

(71) Applicant: ZINCURE CORP., Seoul (KR)

(72) Inventors: Yang-Hee Kim, Seoul (KR); Jae Won Eom, Guri-si (KR); Sang Won Suh, Chuncheon-si (KR); Bo Young Choi, Chuncheon-si (KR)

(73) Assignee: ZINCURE CORP., Seoul (KR)

( * ) Notice: Subject to any disclaimer, the term of this patent is extended or adjusted under 35 U.S.C. 154(b) by 651 days.

(21) Appl. No.: 17/776,693

(22) PCT Filed: Nov. 12, 2020

(86) PCT No.: PCT/KR2020/015932
§ 371 (c)(1),
(2) Date: May 13, 2022

(87) PCT Pub. No.: WO2021/096270
PCT Pub. Date: May 20, 2021

(65) Prior Publication Data
US 2023/0000839 A1     Jan. 5, 2023

(30) Foreign Application Priority Data
Nov. 14, 2019 (KR) .......................... 10-2019-0145709

(51) Int. Cl.
*A61K 31/427* (2006.01)
*A61P 21/00* (2006.01)

(52) U.S. Cl.
CPC ............ *A61K 31/427* (2013.01); *A61P 21/00* (2018.01)

(58) Field of Classification Search
CPC .............................. A61K 31/427; A61P 21/00
See application file for complete search history.

(56) References Cited

U.S. PATENT DOCUMENTS

2019/0167647 A1    6/2019    Kim et al.

FOREIGN PATENT DOCUMENTS

| CN | 104059060 | 9/2014 |
| JP | 2006-513143 | 4/2006 |
| KR | 10-1324647 | 11/2013 |
| KR | 10-2018-0018343 | 2/2018 |
| WO | 2012-080729 | 6/2012 |

OTHER PUBLICATIONS

Jae-Won Eom et al., "AMP-activated protein kinase contributes to zinc-induced neuronal death via activation by LKB1 and induction of Bim in mouse cortical cultures", Molecular Brain (2016) 9:14, Feb. 2016.
Bo Young Choi et al., "Copper/zinc chelation by clioquinol reduces spinal cord white matter damage and behavioral deficits in a murine MOG-induced multiple sclerosis model.", Neurobiology of Disease 54 (2013) 382-391, Jan. 27, 2013.
Youichirou Higashi et al., "Extracellular zinc and microglial phenotype", Biomedical Research on Trace Elements 28 (3): 121-126, Nov. 2017.
Ashutosh K. Mangalam et al., "AMP-Activated Protein Kinase Suppresses Autoimmune Central Nervous System Disease by Regulating M1-Type Macrophage-Th17 Axis", The Journal of Immunology, 2016; 197:747-760, Jun. 27, 2016.
Jae-Won Eom et al., "Identifying New AMP-Activated Protein Kinase Inhibitors That Protect against Ischemic Brain Injury", ACS Chem. Neurosci. 2019, 10, 2345-2354, Feb. 14, 2019.
Bo Young Choi et al., "A Novel Zinc Chelator, 1H10, Ameliorates Experimental Autoimmune Encephalomyelitis by Modulating Zinc Toxicity and AMPK Activation", International Journal of Molecular Sciences, 2020, 21, 3375; doi:10.3390/ijms21093375, May 10, 2020.

*Primary Examiner* — Kamal A Saeed
(74) *Attorney, Agent, or Firm* — LEX IP MEISTER, PLLC

(57) ABSTRACT

The present invention provides a pharmaceutical composition for treating multiple sclerosis based on AMPK inhibitory function and zinc homeostasis controlling function that effectively treats multiple sclerosis due to its excellent neuroprotective effect without side effects.

2 Claims, 28 Drawing Sheets

PHARMACEUTICAL COMPOSITION FOR TREATING MULTIPLE SCLEROSIS ON BASIS OF AMPK INHIBITORY FUNCTION AND ZINC HOMEOSTASIS CONTROL FUNCTION

STATEMENT OF GOVERNMENT INTEREST

This patent application was supported by the Ministry of SMEs and Startups, and conducted as a TIPS Startup Support Plan Project (Subject name: A research on the development of post-new drug substances for multiple sclerosis using a chemical compound targeted for regulating zinc homeostasis, subject number: S3136303, research period: 2021 Jul. 1~2023 Jun. 30) by the present applicant under the management of Korea Technology and Information Promotion Agency for SMEs.

TECHNICAL FIELD

The present invention relates to a pharmaceutical composition for treating multiple sclerosis, and more particularly, to a pharmaceutical composition for treating multiple sclerosis based on AMPK inhibitory function and zinc homeostasis control function.

BACKGROUND

Multiple sclerosis (MS) is an autoimmune inflammatory disease of the central nervous system that occurs due to abnormal control of the immune system in the human body and destruction of the myelin sheath surrounding the axon of neurons and is known to be involved in various neurotoxicities. Steroids and immunosuppressants have been mainly used for the treatment of multiple sclerosis, which is based on the fact that the main mechanism of multiple sclerosis is an autoimmune mechanism. It is an attempt to control the disease by weakening the body's immune function. However, studies to date have shown that, although these treatments have a prominent effect in the acute phase of the disease, they do not play a role in inhibiting or reducing the recurrence of the disease in the long term. Therefore, to this date, the most known effective therapy is injecting a large amount of steroids or immunosuppressants at regular intervals over several days in the acute phase. In recent years, many attempts have been made to inject beta-globulin through the spinal fluid or the skin to alleviate chronic degeneration by preventing recurrence of this disease. However, a drawback is that one should continue to receive the treatment.

On the other hand, it has been reported that excessive zinc accumulation or severe deficiency in the body is toxic to neurons, and the homeostatic loss of zinc may cause multiple sclerosis. Recently, various research groups have been conducting research on zinc homeostasis in multiple sclerosis, and various results have been published, but most of them have been results of changes in the phenomenon of homeostatic loss of zinc, and accurate mechanical research is insufficient. In addition, due to methods of measuring zinc and sample diversity, researches on zinc in multiple sclerosis needs to be conducted more closely. In this regard, Korean Patent No. 1324647 discloses a composition for the treatment or prevention of multiple sclerosis and a screening method thereof.

Technical Problems

However, the prior art is drawn to inhibiting functions of NADPH oxidase and/or MMP using LeuSH (L-Leucinethiol) and thus therapeutics for multiple sclerosis based on inhibiting AMPK and controlling zinc neurotoxicity is still untapped.

The present invention is to solve various problems including the above problems, and an object of the present invention is to provide a pharmaceutical composition for treating multiple sclerosis based on AMPK inhibition function and zinc homeostasis control function for effectively treating multiple sclerosis without a side effect. However, this problem is exemplary, and the scope of the present invention is not limited thereto.

SUMMARY

According to one aspect of the present invention, there is provided a pharmaceutical composition for treating multiple sclerosis or encephalomyelitis, containing a compound having a structure of Formula I below as an active ingredient:

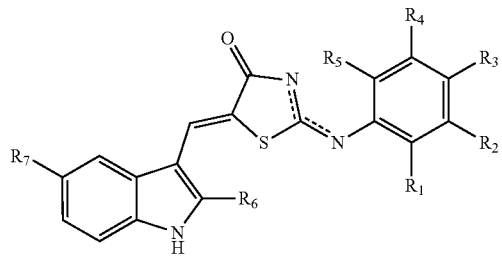

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—$(CH_2)_n$—O— ring (n is an integer of 1 to 3), or a substituted or unsubstituted C6 aromatic ring, $R_6$ is hydrogen or methyl, and $R_7$ is hydrogen or halogen and ⁓⁓⁓⁓ is a single bond or a double bond.)

According to another aspect of the present invention, there is provided a method for treating multiple sclerosis in a subject suffering from multiple sclerosis, comprising administering to the subject a therapeutically effective amount of a compound having the structure of Formula I below:

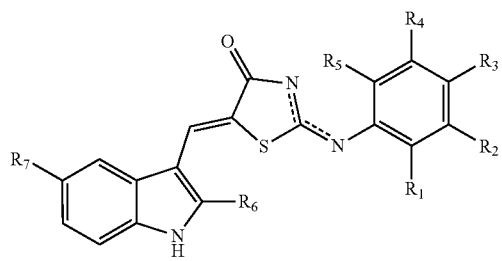

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—$(CH_2)_n$—O— ring (n is an integer of 1 to 3), or a substituted or unsubstituted C6 aromatic ring, $R_6$ is hydrogen or methyl, and $R_7$ is hydrogen or halogen and ⎯⎯⎯⎯⎯ is a single bond or a double bond.)

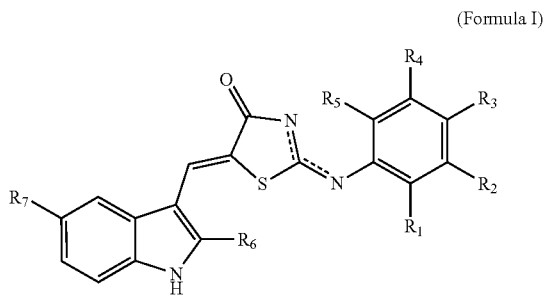

(Formula I)

According to another aspect of the present invention, there is provided a compound having the structure of Formula I below for use in the treatment of multiple sclerosis:

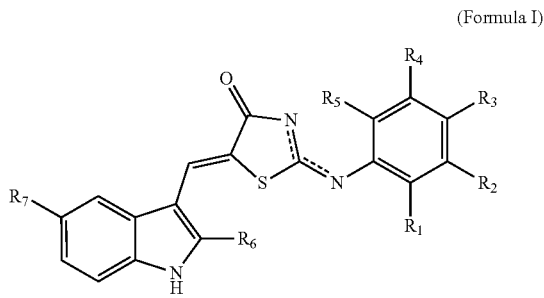

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and R3 together form an —O—$(CH_2)_n$—O— ring (n is an integer of 1 to 3), or a substituted or unsubstituted C6 aromatic ring, $R_6$ is hydrogen or methyl, and $R_7$ is hydrogen or halogen and ⎯⎯⎯⎯⎯ is a single bond or a double bond.)

Effect of the Invention

The pharmaceutical composition for the treatment of multiple sclerosis based on the AMPK inhibitory function and zinc homeostasis control function according to the present invention made as described above can be used for the development of new therapeutic agents that can overcome spinal cord damage and behavioral disorders due to multiple sclerosis by administrating a novel compound having AMPK activity inhibitory function and zinc homeostasis control function. Of course, the scope of the present invention is not limited by these effects.

DETAILED DESCRIPTION OF EMBODIMENTS

Definition of Terms

Figure 1A:
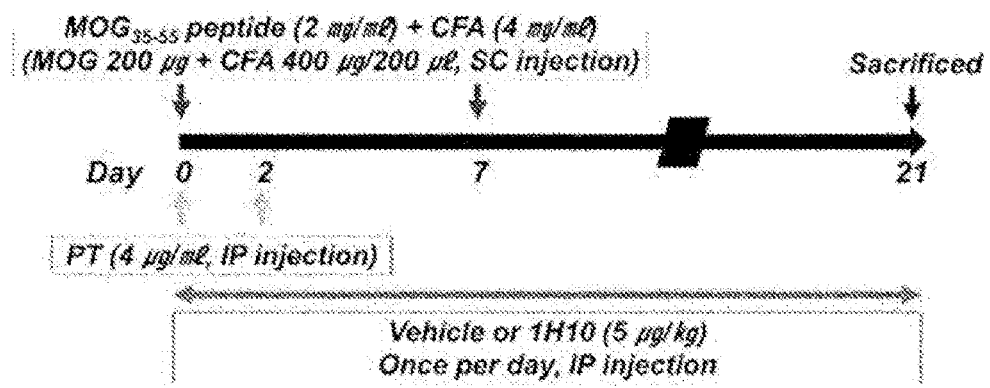
FIG. 1A is a diagram illustrating a timeline for an experimental design according to an embodiment of the present invention. For the entire experimental process, 1H10 was administered intraperitoneally once a day, and the mice were sacrificed on the 21$^{st}$ day after immunization.

As used herein, "AMP-activated protein kinase (AMPK)" is a heterotrimeric protein composed of a catalytic α subunit (α1 or α2) and two regulatory subunits (β and γ). AMPK is phosphorylated and activated when cellular energy levels are low, and in turn regulates cellular metabolism, thereby regulating gene expression over a long period of time to restore ATP levels. Increases in the AMP/ATP ratio, changes in cellular pH and redox state, and increases in the creatine/phosphocreatine ratio are known to activate AMPK.

As used herein, "zinc" is a metal element abundantly present throughout the body, including the central nervous system, and plays a very important role in synaptic plasticity and learning and memory of neurons. However, it is well known that excessive zinc accumulation or severe deficiency is toxic to neurons. Intracellular accumulation of zinc is a major cause of nerve damage that occurs after acute neurological diseases such as stroke, epilepsy, traumatic brain injury, and hypoglycemia and it causes the formation of plaques generated in Alzheimer's brain, a chronic disease.

DETAILED DESCRIPTION OF THE INVENTION

According to one aspect of the present invention, there is provided a pharmaceutical composition for treating multiple sclerosis or encephalomyelitis, containing a compound having a structure of Formula I below as an active ingredient:

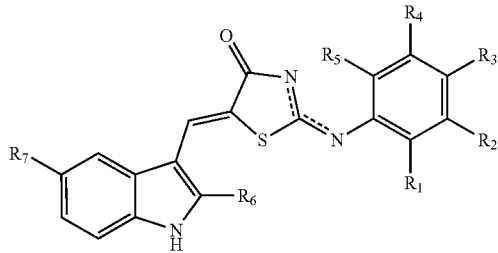

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—$(CH_2)_n$—O— ring (n is an integer of 1 to 3), or a substituted or unsubstituted C6 aromatic ring, $R_6$ is hydrogen or methyl, and $R_7$ is hydrogen or halogen and ⁓⁓⁓⁓ is a single bond or a double bond.)

In the above composition, the unsubstituted alkyl group may be methyl, ethyl, propyl or butyl and the substituted alkyl group may be a fluoromethyl, difluoromethyl, trifluoromethyl group, chloromethyl, dichloromethyl, trichloromethyl, iodomethyl, diiodomethyl, or triraiodomethyl, and the halogen may be fluorine (F), chlorine (Cl), bromine (Br) or iodine (I).

In the above composition, the compound may be
(5Z)-5-(1H-Indol-3-ylmethylene)-2-[2-(trifluoromethyl)phenyl]amino-1,3-thiazol-4(5H)-one,
(5Z)-5-(1H-Indol-3-ylmethylene)-2-[3-(trifluoromethyl)phenyl]amino-1,3-thiazol-4(5H)-one,
(5Z)-2-[(3-Bromophenyl)amino]-5-(1H-indol-3-ylmethylene)-1,3-thiazol-4(5H)-one,
(5Z)-5-(1H-Indol-3-ylmethylene)-2-[(4-methylphenyl)amino]-1,3-thiazol-4(5H)-one,
(5Z)-5-(1H-Indol-3-ylmethylene)-2-[(3-methylphenyl)amino]-1,3-thiazol-4(5H)-one,
(5Z)-2-Anilino-5-(1H-indol-3-ylmethylene)-1,3-thiazol-4(5H)-one,
(5Z)-2-[(2,4-Dimethylphenyl)amino]-5-(1H-indol-3-ylmethylene)-1,3-thiazol-4(5H)-one,
(5Z)-2-[(2-Chlorophenyl)amino]-5-(1H-indol-3-ylmethylene)-1,3-thiazol-4(5H)-one,
(5Z)-2-[(3,4-Dimethylphenyl)amino]-5-(1H-indol-3-ylmethylene)-1,3-thiazol-4(5H)-one,
(5Z)-2-[(4-Hydroxyphenyl)amino]-5-(1H-indol-3-ylmethylene)-1,3-thiazol-4(5H)-one,
(5Z)-5-(1H-Indol-3-ylmethylene)-2-[(2-methylphenyl)amino]-1,3-thiazol-4(5H)-one,
(5Z)-2-[(2,3-Dimethylphenyl)amino]-5-(1H-indol-3-ylmethylene)-1,3-thiazol-4(5H)-one,
(5E)-5-(1H-Indol-3-ylmethylene)-2-(1-naphthylamino)-1,3-thiazol-4(5H)-one,
(5Z)-2-[(3-Chlorophenyl)amino]-5-(1H-indol-3-ylmethylene)-1,3-thiazol-4(5H)-one,
(5E)-2-Anilino-5-[(5-bromo-1H-indol-3-yl)methylene]-1,3-thiazol-4(5H)-one,
(5E)-2-[(4-Butylphenyl)amino]-5-(1H-indol-3-ylmethylene)-1,3-thiazol-4(5H)-one,
(5Z)-2-[(4-Butylphenyl)amino]-5-(1H-indol-3-ylmethylene)-1,3-thiazol-4(5H)-one,
(5Z)-5-(1H-Indol-3-ylmethylene)-2-[(3-methoxyphenyl)amino]-1,3-thiazol-4(5H)-one,
(5Z)-5-[(2-Methyl-1H-indol-3-yl)methylene]-2-[(4-methylphenyl)amino]-1,3-thiazol-4(5H)-one,
(5E)-5-[(2-Methyl-1H-indol-3-yl)methylene]-2-[(4-methylphenyl)amino]-1,3-thiazol-4(5H)-one,
3-[(5Z)-5-(1H-Indol-3-ylmethylene)-4-oxo-4,5-dihydro-1,3-thiazol-2-yl]aminobenzoic acid,
2-[(5E)-5-(1H-Indol-3-ylmethylene)-4-oxo-4,5-dihydro-1,3-thiazol-2-yl]aminobenzoic acid,
(5Z)-2-[(2-Chlorophenyl)amino]-5-[(2-methyl-1H-indol-3-yl)methylene]-1,3-thiazol-4(5H)-one,
2-Hydroxy-5-[(5Z)-5-(1H-indol-3-ylmethylene)-4-oxo-4,5-dihydro-1,3-thiazol-2-yl]aminobenzo is acid,
(2E,5E)-5-((5-bromo-1H-indol-3-yl)methylene)-2-(phenylimino)thiazolidin-4-one,
(2Z,5E)-5-((1H-indol-3-yl)methylene)-2-((4-butylphenyl)imino)thiazolidin-4-one,
(Z)-5-((1H-indol-3-yl)methylene)-2-((4-butylphenyl)amino)thiazol-4(5H)-one,
(Z)-5-((1H-indol-3-yl)methylene)-2-((3-methoxyphenyl)amino)thiazol-4(5H)-one,
(2E,5Z)-5-((2-methyl-1H-indol-3-yl)methylene)-2-(p-tolylimino)thiazolidin-4-one,
(2Z,5E)-5-((2-methyl-1H-indol-3-yl)methylene)-2-(p-tolylimino)thiazolidin-4-one,
(Z)-3-((5-((1H-indol-3-yl)methylene)-4-oxo-4,5-dihydrothiazol-2-yl)amino)benzoic acid,
(E)-2-((5-((1H-indol-3-yl)methylene)-4-oxo-4,5-dihydrothiazol-2-yl)amino)benzoic acid,
(2Z,5Z)-2-((2-chlorophenyl)imino)-5-((2-methyl-1H-indol-3-yl)methylene)thiazolidin-4-one,
(Z)-5-((5-((1H-indol-3-yl)methylene)-4-oxo-4,5-dihydrothiazol-2-yl)amino)-2-hydroxybenzoic acid or
(Z)-5-((1H-indol-3-yl)methylene)-N-(benzo[d][1,3]dioxol-5-yl)-4-methylene-4,5-dihydrothiazol-2-amine.

In the composition, the compound may have anti-demyelination effect, neuroprotective effect, anti-apoptotic effect or anti-inflammatory infiltration effect.

According to another aspect of the present invention, there is provided a method for treating multiple sclerosis in a subject suffering from multiple sclerosis, comprising administering to the subject a therapeutically effective amount of a compound having the structure of Formula I below:

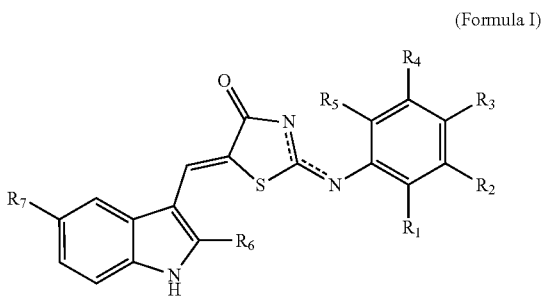

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—(CH$_2$)$_n$—O— ring (n is an integer of 1 to 3), or a substituted or unsubstituted C6 aromatic ring, $R_6$ is hydrogen or methyl, and $R_7$ is hydrogen or halogen and ═══ is a single bond or a double bond.)

According to another aspect of the present invention, there is provided a method for treating encephalomyelitis in a subject suffering from encephalomyelitis, comprising administering to the subject a therapeutically effective amount of a compound having the structure of Formula I below:

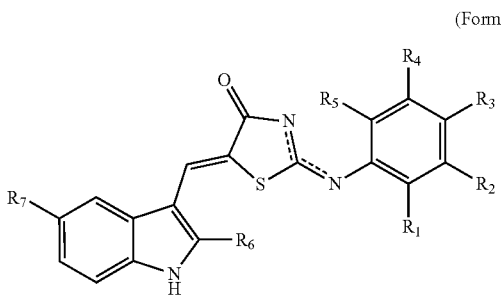

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—(CH$_2$)$_n$—O— ring (n is an integer of 1 to 3), or a substituted or unsubstituted C6 aromatic ring, $R_6$ is hydrogen or methyl, and $R_7$ is hydrogen or halogen and ═══ is a single bond or a double bond.)

According to another aspect of the present invention, there is provided a compound having the structure of Formula I below for use in the treatment of multiple sclerosis:

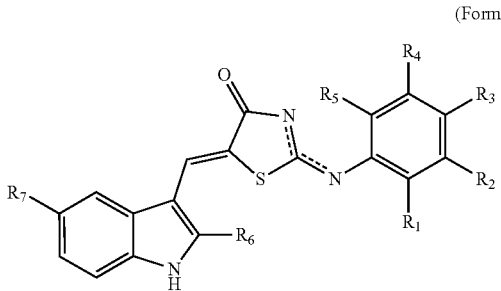

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—(CH$_2$)$_n$—O— ring (n is an integer of 1 to 3), or a substituted or unsubstituted C6 aromatic ring, $R_6$ is hydrogen or methyl, and $R_7$ is hydrogen or halogen and ═══ is a single bond or a double bond.)

According to another aspect of the present invention, there is provided a compound having the structure of Formula I below for use in the treatment of encephalomyelitis:

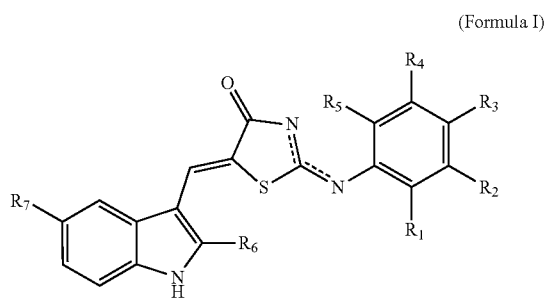

(Formula I)

(In the above Formula, $R_1$ to $R_5$ are each independently hydrogen, a hydroxyl group, a halogen, a C1-7 substituted or unsubstituted alkyl group, an amine group, a carboxyl group, and $R_2$ and $R_3$ together form an —O—(CH$_2$)$_n$—O— ring (n is an integer of 1 to 3), or a substituted or unsubstituted C6 aromatic ring, $R_6$ is hydrogen or methyl, and $R_7$ is hydrogen or halogen and ═══ is a single bond or a double bond.)

The effective amount of the compound in the pharmaceutical composition of the present invention may vary depending on the type of the patient's lesion, application site, and number of treatments, treatment time, dosage form, patient's condition, type of adjuvant, and the like. The amount used is not particularly limited, but may be 0.01 µg/kg/day to 10 mg/kg/day. The daily dose may be administered once a day, or dividedly administered 2-3 times a day at an appropriate interval, or may be administered intermittently at intervals of several days.

In the pharmaceutical composition of the present invention, the compound may be contained in an amount of 0.1-100% by weight based on the total weight of the composition. The pharmaceutical composition of the present invention may further include suitable carriers, excipients and diluents commonly used in the preparation of pharmaceutical compositions. In addition, additives for solid or liquid formulations may be used in the preparation of the pharmaceutical composition. The additive for formulation may be either organic or inorganic.

Examples of the excipient include lactose, sucrose, sucrose, glucose, cornstarch, starch, talc, sorbit, crystalline cellulose, dextrin, kaolin, calcium carbonate and silicon dioxide. Examples of the binder include polyvinyl alcohol, polyvinyl ether, ethyl cellulose, methyl cellulose, gum arabic, tragacanth, gelatin, shellac, hydroxypropyl cellulose, hydroxypropyl methyl cellulose, calcium citrate, and dextrin and pectin. Examples of the lubricant include magnesium stearate, talc, polyethylene glycol, silica, and hydrogenated vegetable oil. As a coloring agent, if it is permitted to be added to pharmaceuticals normally, anyone can be used. These tablets and granules may be coated with sugar coating, gelatin coating, or other appropriate coatings as needed. In addition, preservatives, antioxidants, etc. may be added as needed.

The pharmaceutical composition of the present invention may be prepared in any formulation conventionally used in the art (eg, Remington's Pharmaceutical Science, latest edition; Mack Publishing Company, Easton PA), and the type of the formulation is not particularly limited. These formulations are described in Remington's Pharmaceutical Science, 15$^{th}$ Edition, 1975, Mack Publishing Company, Easton, Pennsylvania 18042 (Chapter 87: Blaug, Seymour), a recipe commonly known to all pharmaceutical chemistry.

In the pharmaceutical composition of the present invention, the compound can be administered orally or parenterally, and preferably parenterally including intravenous injection, subcutaneous injection, intracerebroventricular injection, intracerebrospinal fluid injection, intramuscular injection and intraperitoneal injection.

Figure 7:
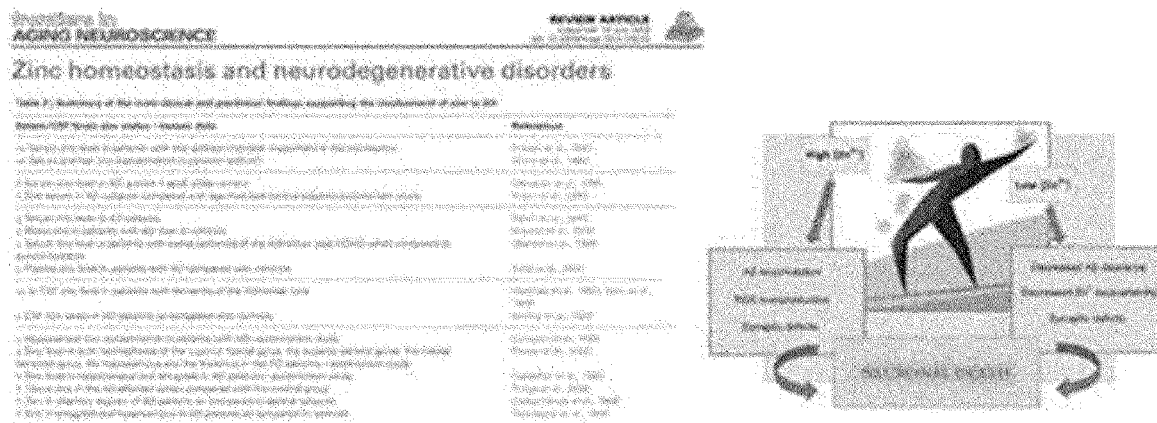
FIG. 7 is a diagram illustrating research results showing that homeostatic loss of zinc may cause multiple sclerosis.

Although many drugs and treatments have been developed so far for the treatment of multiple sclerosis, a degenerative nervous system disease, they are still not very effective. Recently, many researchers have been conducting researches on how to prevent harmful immune cell infiltration into the brain as one of the phenomena that appears in multiple sclerosis. Interest in the correlation between zinc and multiple sclerosis is increasing as results of inhibiting symptoms of multiple sclerosis and tissue damage of spinal white matter are reported in mice that genetically remove zinc transport 3 (ZnT3), which controls synaptic vesicle movement at the end of the nerve and administrating zinc chelatores. In addition, it has been reported that in this process, the production of active oxygen species due to activation of NADPH oxidase is involved in the secondary damage of meylin occurring in multiple sclerosis. Therefore, according to the results of several recently published studies, it is known that zinc is secreted from the cell terminal and then accumulated in the cytoplasm, thereby damaging myelin due to the toxicity of zinc released from protein (FIG. 7). In the previous study of the present inventors, it was reported that demyelination and microglia activity were reduced and T cell infiltration that cause encephalitis was inhibitored, which are symptoms of EAE in animals in which the gene encoding zinc transporter 3 (ZnT3), which is involved in zinc transport into synaptic vesicles, was genetically removed, or when Clioquinol (CQ), a zinc chelator was administrated. The preceding studies are as follows, respectively: Choi, B. Y. et al., *Neurobiol. Dis.* 54: 382-391, 2013; Choi, B. Y. et al., *J. Neuroinflammation.* 12: 104, 2015; Choi, B. Y. et al., *Neurobiol. Dis.* 94: 205-212, 2016).

Figure 8:
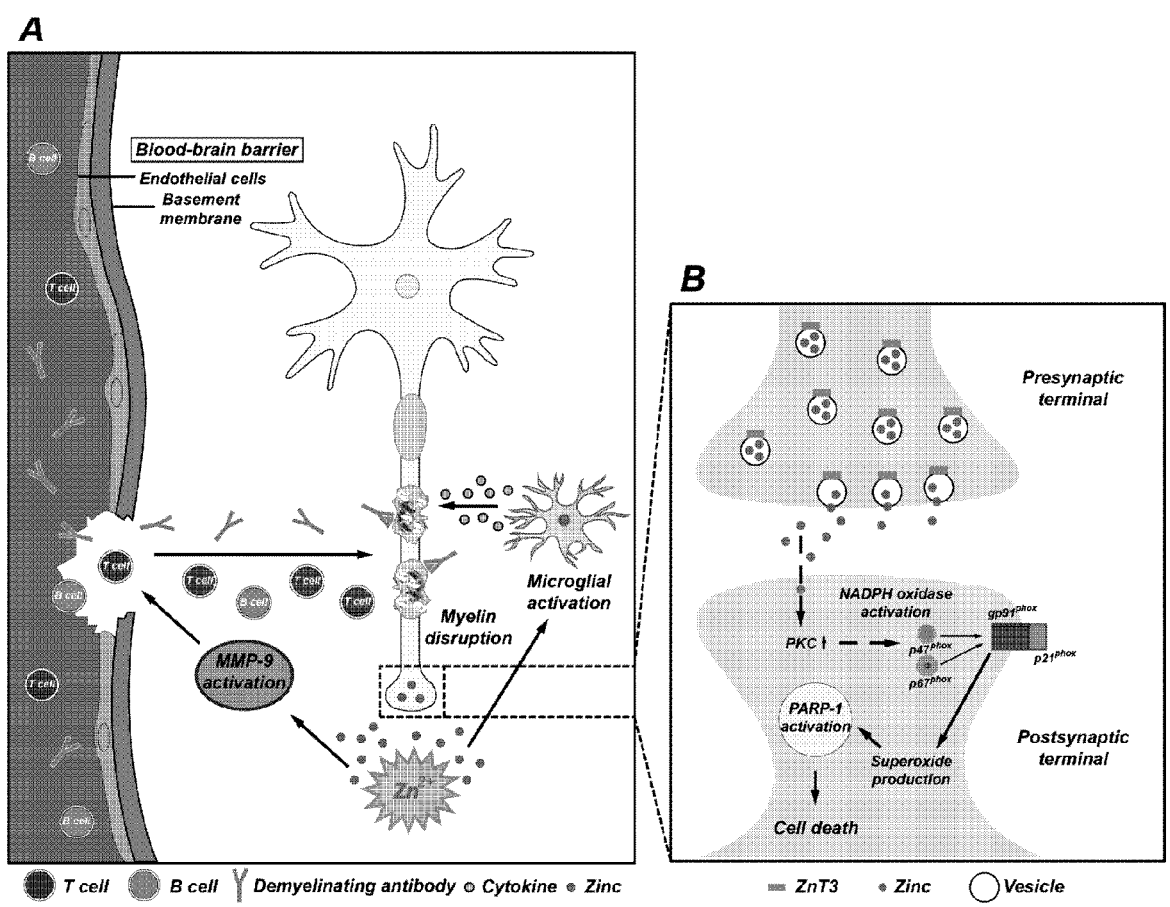
FIG. 8 is a diagram schematically illustrating a possible association between pathology of multiple sclerosis (MS) and zinc.

In addition, nerve cell damage processes such as zinc neurotoxicity and excitotoxicity are accompanied by a decrease in ATP and an increase in AMP, so that AMPK activity activated by AMP is clearly shown (Eom, J. W. et al., *Mol. Brain.* 9: 14, 2016). The present inventors conducted a study to identify the cell death mechanism related to AMPK in the process of brain nerve cell damage, and reported the related mechanism in Molecular Brain (IF: 3.410) in 2016. In addition, according to the results of several recently published studies, it has been reported that AMPK activity is associated with damage and pathological involvement of the central nervous system in neurodegenerative diseases such as dementia, Parkinson's disease, Huntington's chorea, and multiple sclerosis. Accordingly, the present inventors have conducted a study on the AMPK-based neurotoxic mechanism, which is the most essential for metabolic regulation. Based on the previous research, the present inventors conducted research on the development of a novel AMPK inhibitor and screened a new compound to obtain an AMPK inhibitor ((Z)-5-((1H-indol-3-yl)methylene)-2-((3-hydroxyphenyl)amino)thiazol-4(5H)-one, named "1H10", Formula II) was discovered, and thereafter from the studying the mechanism of action (MOA) of drugs, the present inventors reported that 1H10 reduced neuronal cell death caused by zinc toxicity, excitory toxicity, and oxidartive damage, etc. after stroke by regulating the concentration of free zinc in the cell (Eom J. W. et al., *ACS Chem Neurosci.* 10(5): 2345-2354, 2019, FIG. 8).

(Formula II)

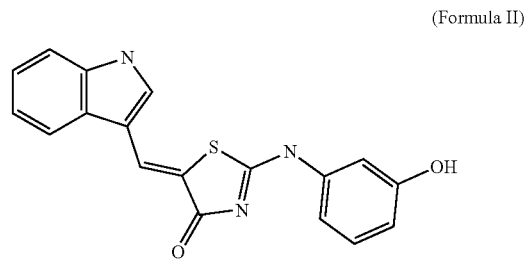 [SMILES: O=C1N=C(Nc2cccc(O)c2)S/C1=C\c1c[nH]c2ccccc12]

The present invention has shown that after induction of experimental autoimmune encephalomyelitis (EAE), which is an animal model for multiple sclerosis, the 1H10 can suppress the onset of diseases at various levels. Specifically, according to 1H10 treatment, the behavioral experiment showed excellent symptom relief effects and the incidence was also suppressed. In addition, it was confirmed that demyelination of the spinal cord, immune cell activity was reduced, and infiltration of immune cells into the area where demyelination has progress was suppress. These results suggest that the effect is related to the mechanism of inhibiting AMPK activity of the 1H10 compound. In addition, it was confirmed that zinc accumulation in the spinal cord white matter was reduced according to 1H10 treatment, thereby inhibiting MMP-9 and preventing accumulation of immune cells accordingly, and it was observed that 1H10 could act directly on zinc and chelate it. Finally, it was demonstrated that the effectiveness of 1H10 was excellent even in the long-term EAE model administered up to 45 days.

Therefore, the pharmaceutical composition for treating multiple sclerosis based on the AMPK inhibitory function and the zinc homeostasis control function of the present invention provides a new therapeutic agent capable of overcoming spinal cord damage and behavioral disorders caused by multiple sclerosis by treating a novel compound with AMPK inhibiting and zinc homeostasis control function. The novel drug may function as a zinc chelator in a process of nerve cell damage, and in particular, 1H10 may function as a zinc ionophore as well as a zinc chelator, and thus may be developed as an active agent for controlling zinc homeostasis.

Hereinafter, the present invention will be described in more detail through following examples and experimental examples. However, the present invention is not limited to the following examples and experimental examples, but may be implemented in various different forms, and the following examples and experimental examples are provided to complete the present invention and to completely inform those skilled in the art the scope of the present invention.

General Methods
Materials

The experimental animals used in the present invention are an 8-week-old, C57BL/6 female mice supplied from Dae Han BioLink, Co., Ltd. (Korea). These mice were bred in an environment controlled by temperature and humidity, and feed and water were fed freely.

Culturing of Cerebral Cortex Neurons

The mouse cortical neurons used in the present invention were extracted from the brain of a mouse embryo, and cultured in Dulbecco's modified Eagle's medium (DMEM, Gibco, Grand Island, NY, US) supplemented with 5% fetal bovine serum (FBS) and 5% horse serum (HS) under the condition of 95% humidity, 5% $CO_2$ and 37° C. For activation and differentiation of the cells, the cells were grown to a density of $2 \times 10^4$ cells in a 24-well tissue culture plate and cultured in MEM medium without FBS and HS before treatment with zinc and compounds.

Manufacture of Animal Models of Multiple Sclerosis

The present inventors induced experimental autoimmune encephalomyelitis (EAE), an animal model of multiple sclerosis, by subcutaneously injecting Myelin oligodendrocyte glycoprotein 35-55 (MOG35-55) peptide antigen into C57BL/6 female mice (FIG. 1A). For this, MOG35-55 (Anaspec, USA) and Complete freund's adjuvant (CFA) were first prepared, and MOG35-55 (2 mg/ml) was dissolved in Phosphate buffered saline (lx PBS, Sigma), and then the 25 ml of CFA was prepared by dispending 25 ml of incomplete freund's adjuvant (IFA. Sigma) in a 50 ml conical tube. Then, in a fume hood, *Mycobacterium tuberculosis* H37Ra (100 mg; Difco, USA) was added to the IFA in order to prepare CFA and store it in the refrigerator after vortexing before use. Thereafter, MOG35-55 and CFA containing *Mycobacterium tuberculosis* H37Ra was mixed in the same amount and injected into both flanks of the mice. And then Pertussis toxin (4 μg/ml, List Biological Laboratories, USA) was injected intraperitoneally on the day of immunization and on the second day after immunization. After the immunization, the mice's body weight and clinical symptoms were measured every day, and the degree of EAE progression was evaluated based on specific clinical symptoms. More details on this are provided below.

EAE Clinical Symptom Assessment

EAE clinical symptom was evaluated based on previous studies (Jones et al., *J. Neuroimmunol.* 199(1-2): 83-93. 2008). Specifically, for the evaluation of clinical symptoms of EAE, the behavior of mice was evaluated daily according to the following criteria. score 0, no symptoms; score 0.5, partial paralysis of tail or slight abnormal gait; score 1.0, complete or partial tail paralysis and mild hindlimb weakness; score 1.5, complete tail paralysis and mild hindlimb weakness; score 2.0, tail paralysis and moderate hindlimb weakness (proved by frequent foot loss while walking on cage); score 2.5, hind limb weight loss but slight movement; score 3.0, complete hindlimb paralysis; score 3.5, hindlimb paralysis and mild weakness in forelimbs; score 4.0, completely paralyzed in the extremities but moving the head; score 4.5, moribund; score 5.0, death.

Cresyl Violet Staining

On the $21^{st}$ day after EAE induction, the present inventors anesthetized mice with urethane, and then perfused 4% paraformaldehyde into the heart to fix the spinal cord. After extracting the spinal cord, infiltration of mononuclear cells in the spinal cord was observed through cresyl violet staining. To this end, first, the spinal cord was sliced in a cryostat to a thickness of 30 μm to obtain a cryosection, and then placed on a gelatin-coated slide and dried at room temperature for 30 minutes. After immersing in 100% and 70% ethanol solutions for 3 minutes each in sequence, they were stained in 0.1% cresyl violet solution for 15 minutes. Then, they were washed with tap water to remove the excessively dyed area, dehydrated in 50%, 70%, 80%, 90%, and 100% ethanol solution for 3-5 minutes each, and after two transparent processes in xylene for 15 minutes each, they were embedded and observed with an optical microscope.

Immunohistochemistry

On the $21^{st}$ day after EAE induction, the present inventors anesthetized mice with urethane and then perfused 4% paraformaldehyde into the heart to fix the spinal cord. And then, an immunohistochemistry was performed using anti-CD4, anti-CD8, and anti-CD20 antibodies used as markers for T cells. Cryosections were reacted with 3% hydrogen peroxide at room temperature for 15 minutes to remove endogenous peroxidase, and then primary antibodies, rat anti-CD4 (1:50, BD Bioscience, CA, USA), anti-CD8 (1:50, BD Bioscience) and goat anti-CD20 (1:50, SantaCruz Biotechnology, USA) antibodies were reacted for 15 hours at 4° C. Thereafter, biotinylated anti-rat IgG or anti-goat IgG (1:250, Vector Laboratories, USA) was reacted at room temperature for 2 hours. Then, it was reacted with avidin-biotin peroxidase conjugate (ABC regent, Vector Laboratories) for 2 hours at room temperature, and the tissues were colored in 3,3'-diaminobenzidine (DAB, Vector Laboratories) solution. In addition, the leakage of Immunoglobulin G (IgG) in the serum was confirmed in order to measure the damage of the blood-brain barrier caused by EAE. The IgG is the most abundant immunoglobulin in plasma, and it is easy to identify it, so the presence of IgG in the spinal cord is used to monitor damage of the blood-brain barrier and extravasation of proteins (Ruth and Feinerman, *Acta Neuropathol.* 76(4): 380-387, 1988). And then, the cryosections were reacted with biotinylated horse anti-mouse IgG (1:250, Vector Laboratories, USA) at room temperature for 2 hours, then reacted with ABC regent in the same way as above, and then colored with DAB solution. Between each step, it was thoroughly washed with PBS, and after dehydration and transparent process using ethanol and xylene, respectively, they were embodied and observed with an optical microscope. Image J program (National Institute of Health, USA) was used for the analysis.

Immunofluorescence Staining

On the $21^{st}$ day after EAE induction, the present inventors anesthetized mice with urethane and then perfused 4% paraformaldehyde into the heart to fix the spinal cord. After extracting the spinal cord, in order to examine demyelination of activity of microglia/macrophages the cell/macrophage activity of the tissue, immunofluorescence staining was performed with anti-myelin basic protein (MBP) and anti-F4/80 (Microglia/Macrophage) antibodies. In addition, anti-bodies against ionized calcium binding adapter molecule-1 (Iba-1) and anti-CD68 (Cluster of Differentiation 68) used as markers of microglia/macrophages to analyze the phenotype of strongly activated microglia/macrophages in the white matter part of the damaged spinal cord. Double immunofluorescence staining was performed using antibodies against CD8 and matrix metalloproteinase 9 (MMP-9) in order to investigate how AMP-activated protein kinase (AMPK) activity affects the survival of these cells. In addition, double immunofluorescence staining was performed using anti-CD8 and anti-phospho-AMPK antibodies to determine how AMP-activated protein kinase (AMPK) activity affects the survival of these cells in T cells infiltrating the spinal cord. In order to compare and analyze the activity of (MMP-9), immunofluorescence staining was performed using anti-MMP-9 antibodies. To examine the activity of astrocytes in the spinal cord, immunofluorescence staining was performed using anti-glial fibrillary acidic protein (GFAP) antibodies. To compare and analyze the expression of cytokines such as tumor necrosis factor (TNF) alpha and interferon (IFN) gamma, double immunofluorescence staining was performed using anti-TNF-alpha and anti-IFN gamma antibodies. In the same manner as the immunohistochemical method described above, the cryosections were reacted with 3% hydrogen peroxide at room temperature for 15 minutes to remove endogenous peroxidase, and then the primary antibodies, rat anti-MBP (1:200, Abcam, UK), anti-F4/80 (1:100, eBioscience, USA), goat anti-Iba1 (1:500, Abcam), anti-CD68 (1:100, Bio-Rad Laboratories, USA), anti-CD8 (1:50, BD Bioscience), anti-p-AMPK (1:100, Abcam), anti-MMP-9 (1:100, Abcam), anti-GFAP (1:500, Abcam), anti-IFN gamma (1:100, Invitrogen, USA), anti-TNF alpha (1:250, Abcam) antibodies were reacted for 15 hours at 4° C. Then, Alexa Fluor 488-, 594-, 647-conjugated secondary antibodies (1:250, Invitrogen, USA) suitable for the host of each primary antibodies were reacted at room temperature for 2 hours. Between each step, they were thoroughly washed with PBS, and after the transparent process using xylene, it was embedded with DPX and observed with a Confocal Laser Scanning Microscope (Carl Zeiss LSM710, Germany), images at more 3-5 views per mouse were analyzed using the Image J program (NIH, USA).

Zinc Staining (TSQ)

After the evaluation of clinical symptoms in EAE-induced mice, the present inventors examined the spinal cord tissue by the N-(6-methoxy 8 quinolyl) para toluenesulfonamide (TSQ) histochemical method, a zinc staining method. In the normal spinal cord, zinc is present at the axon terminal of the gray matter, and only a very small amount is observed in the white matter. On the $21^{St}$ day after EAE induction, the mice were anesthetized with 5% isoflurane, and the spinal cord was removed without perfusion and rapidly cooled with dry ice. Non-fixed frozen tissues were sectioned at a thickness of 20 μm in a cryostat at −15° C. to obtain cryosections. The cryosections were immediately placed on gelatin-coated slides, dried at room temperature for 30 minutes, immersed in TSQ solution for 60 seconds, and then rinsed with 0.9% saline for 60 seconds. TSQ fluorescence was observed using an Olympus IX70 fluorescence microscope with a wavelength of 360 nm/490 nm and evaluated using an INFINITY3-1 CCD-cooled digital color camera (Lumenera Co., Canada) and INFINITY analysis software.

Zinc Chelation

The present inventors treated FluoZin-3, a substance illuminate fluorescence if it bind to free zinc to cultivated neurons in order to verify the possibility of zinc chelation according to the treatment of 1H10 {(Z)-5-((1H-indol-3-yl)methylene)-2-((3-hydroxyphenyl)amino)thiazol-4(5H)-one} according to an embodiment of the present invention, and then measured cytosolic zinc level in the neurons for 60 min after exposing zinc (300 μM) for 15 minutes and removing the zinc. In addition, 20 μM zinc ($ZnCl_2$) and NewPort Green DCF fluorophore, which emits fluorescence when it bind to zinc, were added to the test tube, and 1H10 of the present invention was treated at various concentrations. Clioquinol, a zinc chelator, and calcium ionophore Phosphorus ionomycin was used as controls.

Experimental Example 1: Clinical Signs and Incidence Rates in Animal Models

Figure 1B:
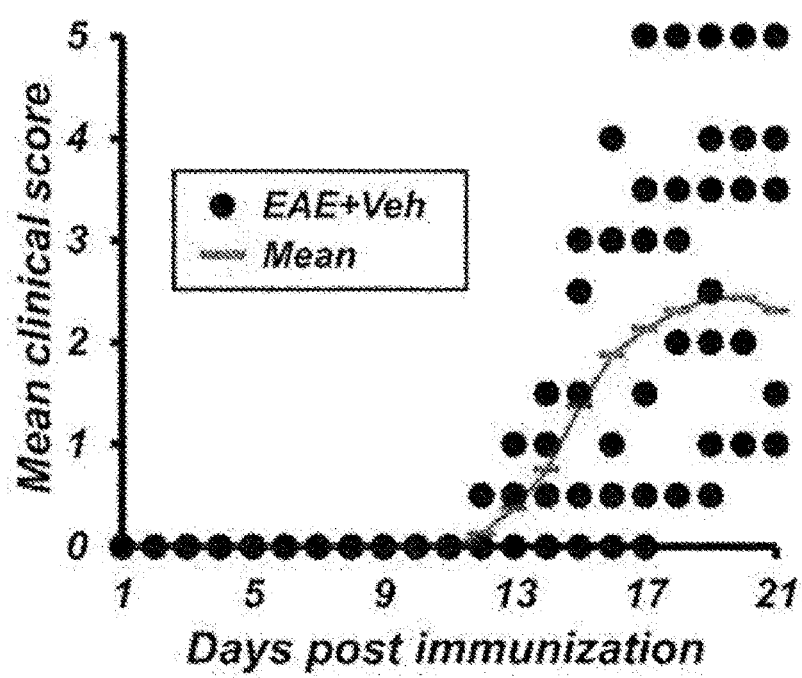
FIG. 1B is a graph representing an analysis of an EAE clinical score for a control group administrated with vehicle only.
Figure 1C:
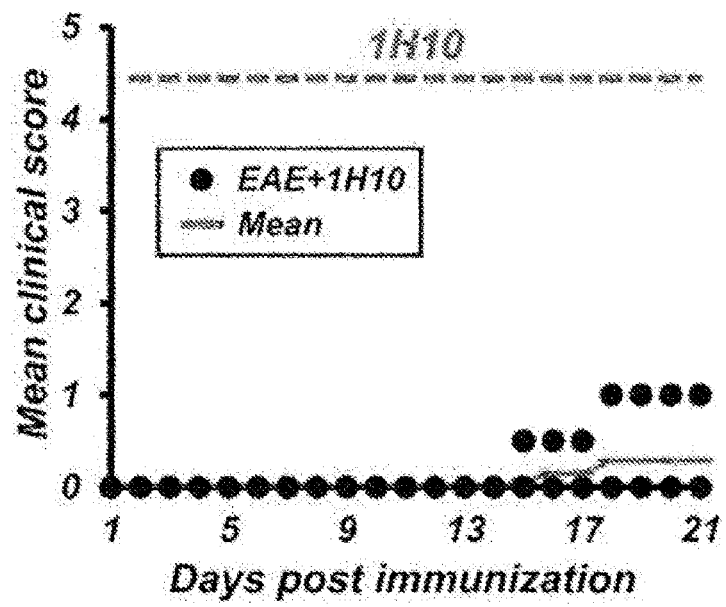
FIG. 1C is a graph representing an analysis of the EAE clinical score for the experimental group administrated with 1H10.

As a result of inducing autoimmune encephalomyelitis, an animal model of multiple sclerosis, according to an embodiment of the present invention, serious behavioral disorders occurred in mice, but the behavioral disorders were significantly inhibited in the experimental group administered with 1H10 of the present invention (FIGS. 1B and 1C). In addition, as a result of evaluating the clinical symptoms of EAE mice, it was observed that in the experimental group administered with 1H10, not only the clinical symptoms but also the incidence rate was suppressed (FIG. 1C).

Figure 1D:
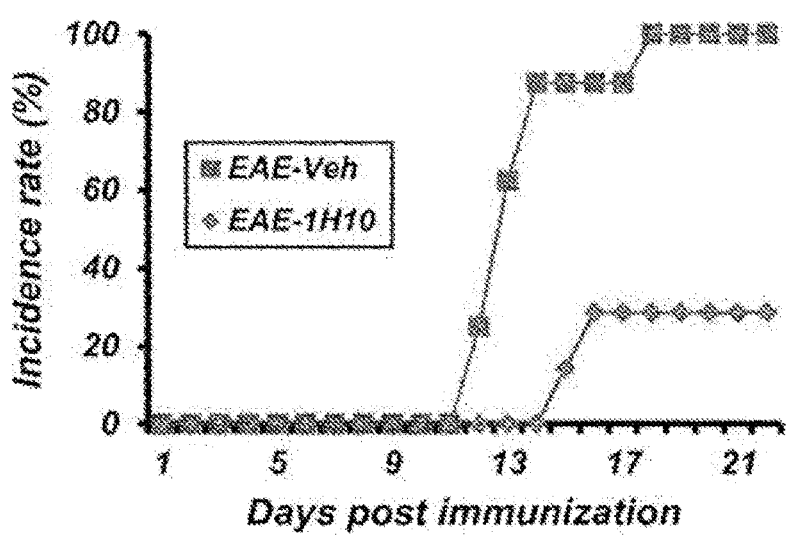
FIG. 1D is a graph representing an analysis of disease incidence rates of vehicle- or 1H10-treated immunized mice. The data are average±SEM (n=7-8 per experimental group). **p<0.05.

These results suggest that 1H10 of the present invention improves the clinical signs and disease progression of myelin oligodendrocyte glycoprotein 35-55 (MOG35-55)-induced EAE (FIG. 1D)

Experimental Example 2: Activity of Microglia/Macrophages

Figure 2A:
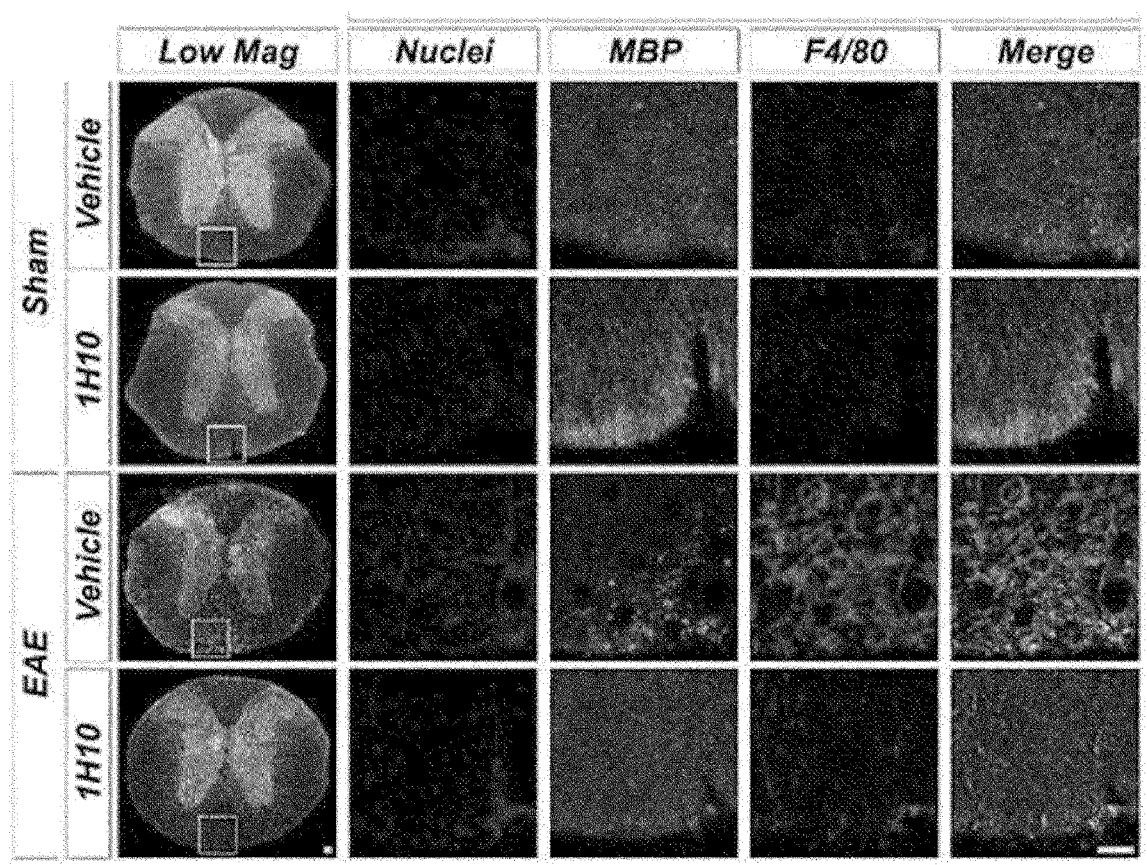
FIG. 2A is a microscopic photograph of typical microglia/ macrophage activation in the spinal cord of sham-operated and MOG35-55 immunized mice (vehicle- or 1H10-treated). F4/80 (red), nuclear stained with DAPI (blue), and demyelinated areas were identified by reduced MBP staining (green). Scale bar, 50 μm.
Figure 2B:
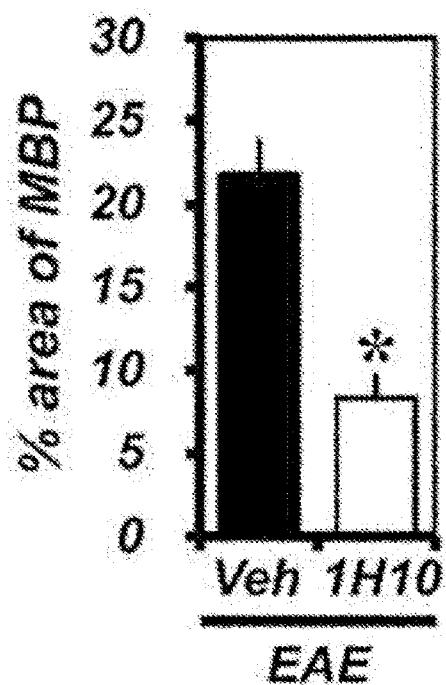
FIG. 2B is a graph representing an analysis of the percentage of MBP immunoreactivity region measured in the same spinal cord region (mean±SEM; n=3-5 per group).
Figure 2C:
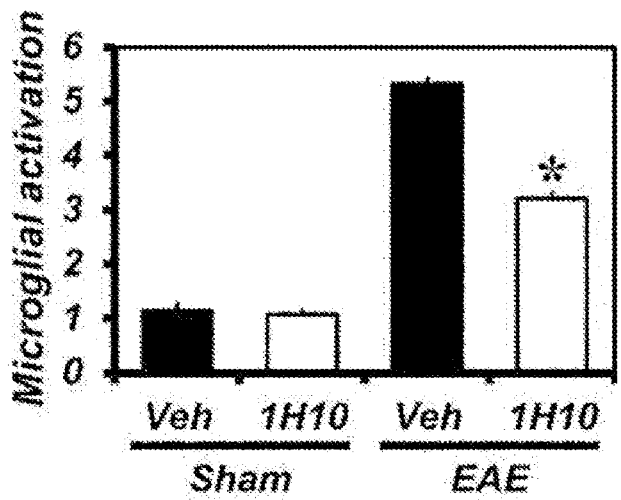
FIG. 2C is a graph representing an analysis of microglia/ macrophage activation ratings measured in the same spinal cord region (mean±SEM; n=3-5 per group).

The present inventors investigated demyelination in the spinal cord and the activity of microglia/macrophages through immunofluorescence staining. As a result, it was confirmed that green signal of the white matter of the spinal cord, which should be stained in green in normal tissues, was reduced in the tissues of EAE mice, and the red color indicating the activity of microglia/macrophages was strongly displayed (FIG. 2A). The decrease in the MBP means that the myelin covering the axon of the nerve is damaged (FIG. 2C). However, the EAE-induced demyelination and activity of microglia/macrophages were significantly decreased in the spinal cord of animals continuously administered with 1H10 (FIG. 2C).

Figure 2D:
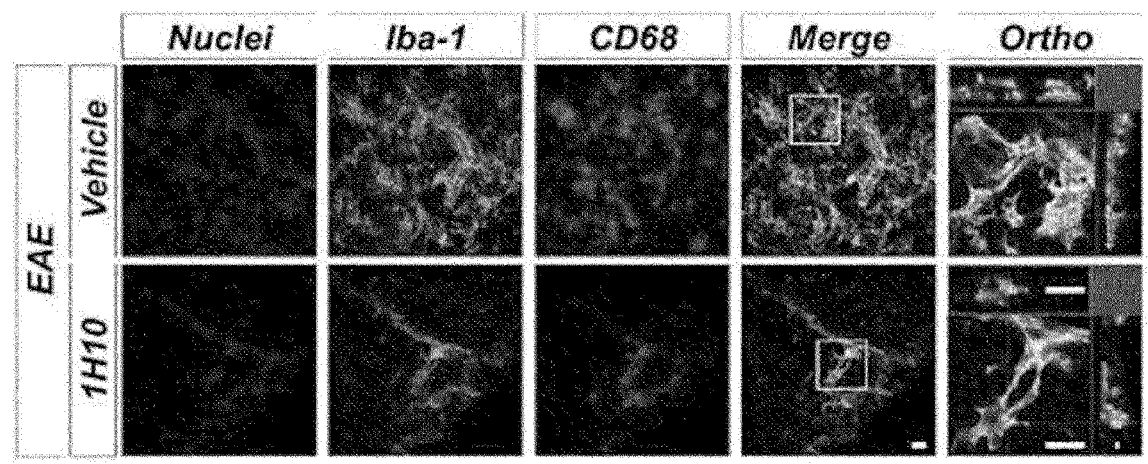
FIG. 2D is a representative image of Iba-1-(green) and CD68-(red)-positive cells as images merged into the vehicle- and 1H10-treated EAE mice. A nucleus stained with DAPI (blue). Scale bar, 50 μm.
Figure 2E:
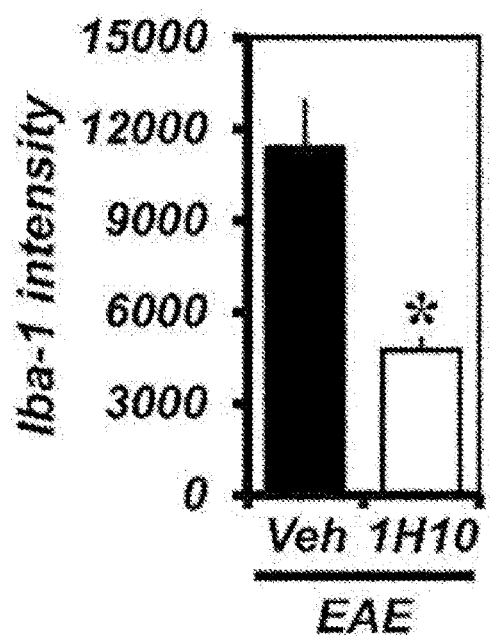
FIG. 2E is a graph representing the quantification (mean±SEM; n=3-5) of the immunofluorescence intensity of Iba-1 determined in the same spinal cord region. **p<0.05.
Figure 2F:
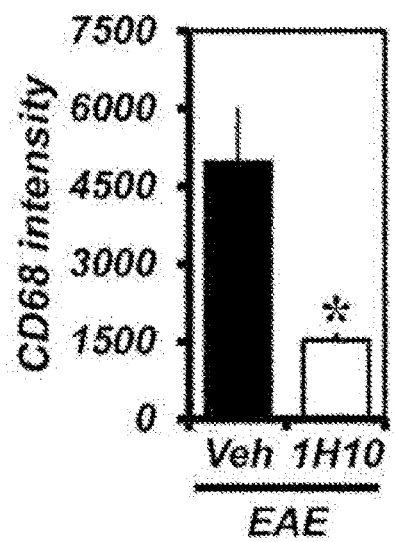
FIG. 2F is a graph representing the quantification of the immunofluorescence intensity of CD68 (F) determined in the same spinal cord region (mean±SEM; n=3-5 per group). **p<0.05.
Figure 2G:
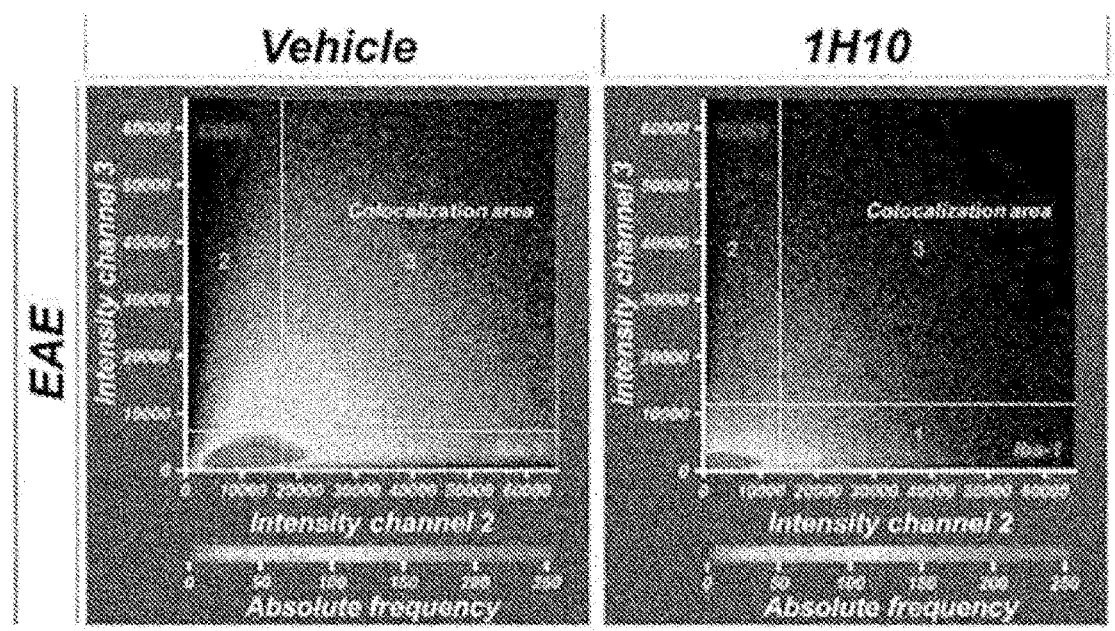
FIG. 2G is a graph representing the colocalization scatterplots of Iba-1 with CD68.
Figure 2H:
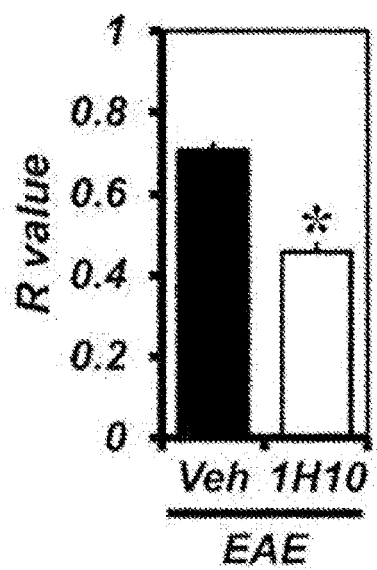
FIG. 2H is a graph representing the quantitative co-localization parameters of Iba-1 using CD68 by measuring the Mander's overlap coefficient and Pearson's correlation coefficient (average±SEM; n=4 per group). **p<0.05.

In addition, as a result of performing double immunofluorescence staining for phenotypic analysis of microglia/macrophages, the simultaneous expression of Iba-1 and CD68 means activated M1-type microglia/macrophages (FIG. 2D) and it was confirmed that the activated M1-type microglia/macrophages were significantly reduced in the group administered with 1H10 after EAE induction (FIGS. 2E to 2H).

Experimental Example 3: Activity of Astrocytes

Figure 17:
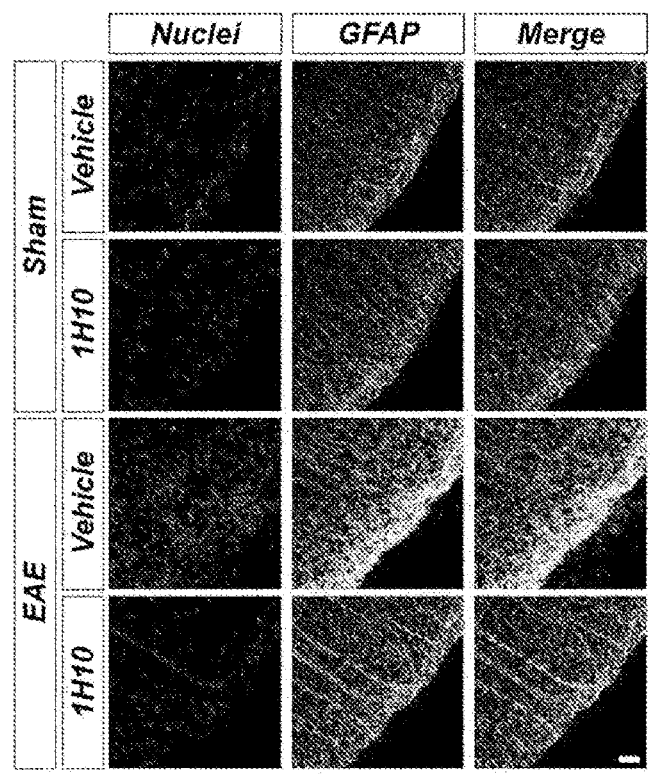
FIG. 17 is a series of immunofluorescence photographs of GFAP (green) as an analysis of the activity of astrocytes in spinal tissue depending on treating 1H10 of the present invention. On Day 21, we observed an abnormal astrogliosis in the spinal cord of the sham-operated and MOG35-55 immunized mice (treated with vehicle only or 1H10). Scale bar, 50 μm
Figure 18:
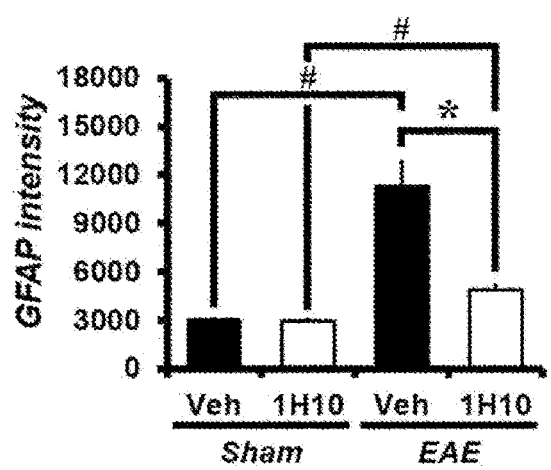
FIG. 18 is a graph representing the quantification of the immunofluorescence intensity of GFAP determined in the same spinal region by analyzing the activity of astrocytes in spinal tissue depending on the treatment of 1H10 according to an embodiment of the present invention (mean±SEM; n=4 per group). *p<0.05 vs. EAE mice treated with vehicle only; #p<0.05 vs. Sham-operated mice (following the Kruskal-Wallis test, Bonferroni post-hoc test: Chi square=11.514, df=3, p=0.009)

The present inventors investigated the activity of astrocytes in the spinal cord tissue through immunofluorescence staining. As a result, it was confirmed that the green color indicating the activity of astrocytes was strongly distributed in the white matter of the spinal cord of the EAE-induced experimental group, whereas the activity of astrocytes was significantly inhibited in the experimental group administered with 1H10 (FIGS. 17 and 18).

Experimental Example 4: AMPK Phosphorylation and EAE-Induced Immune Cell Infiltration The present inventors investigated the infiltration of mononuclear cells in the spinal cord of the mice on the $21^{St}$ day after induction of EAE mice by cresyl violet staining.

Figure 3A:
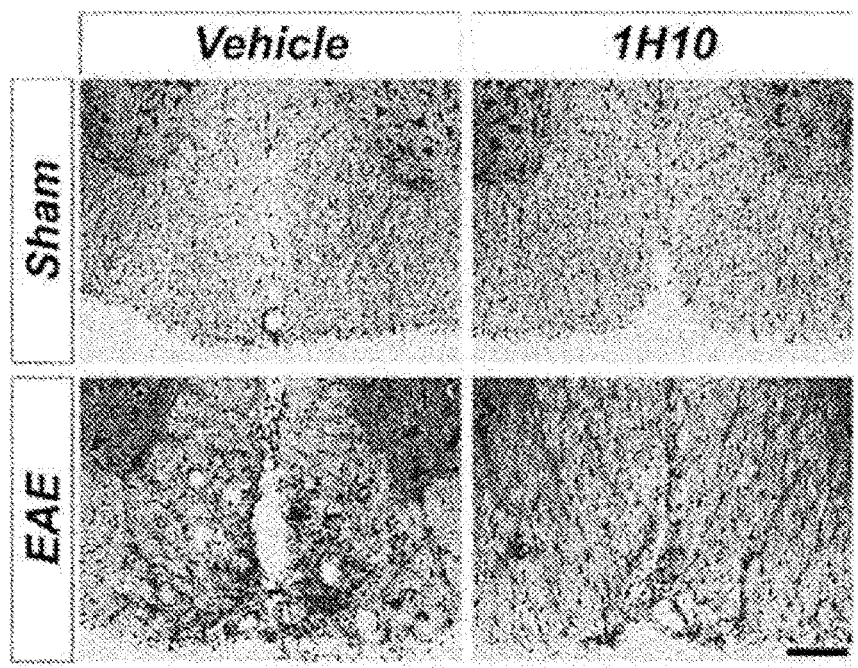
FIG. 3A is a series of microscopic photographs showing sections of the spinal cords stained with cresyl violet to detect infiltration of SMS mononuclear cells. Scale bar, 100 μm.
Figure 3B:
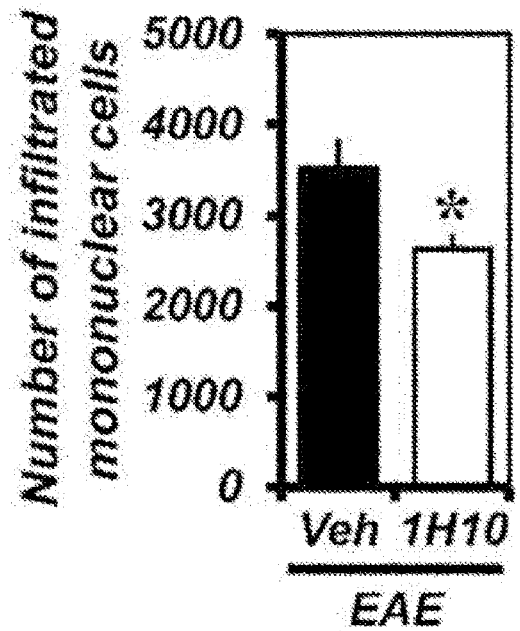
FIG. 3B is a graph representing the quantification of mononuclear cells infiltrated from the spinal cord in mice treated with vehicle or 1H10 at 3 weeks after initial immunization (mean±SEM; n=5 per group). **p<0.05.
Figure 3C:
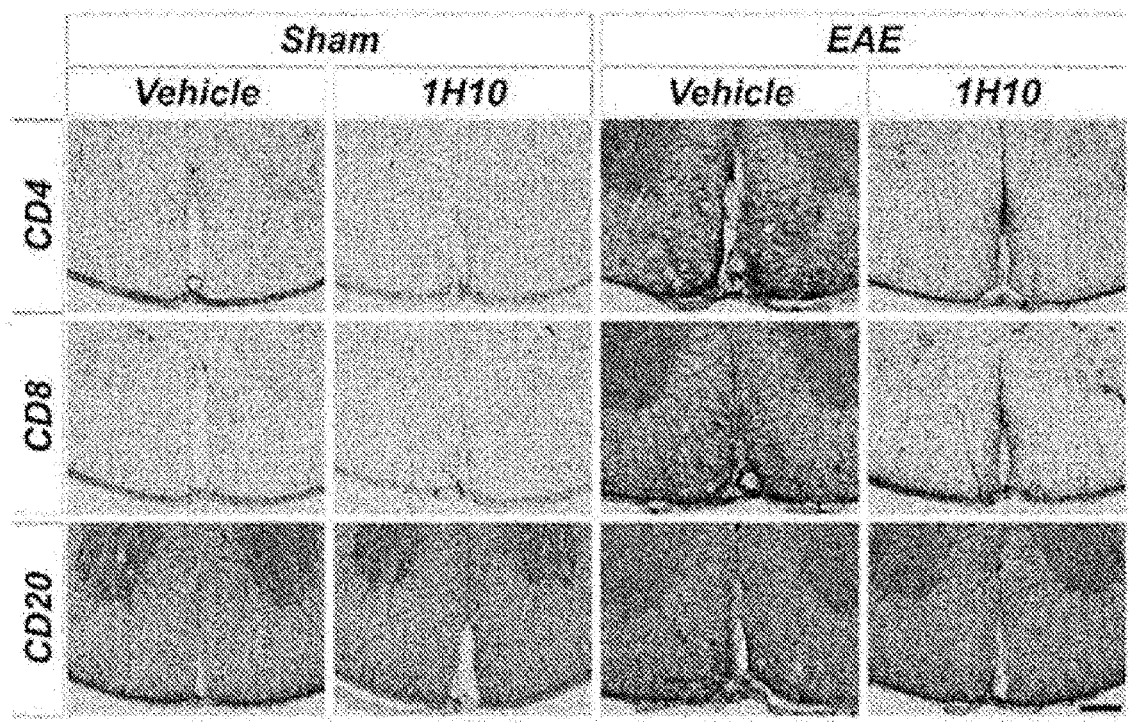
FIG. 3C is a micrograph showing the expression of T and B cells stained with antibodies to cell surface molecules such as CD4, CD8, and CD20.
Figure 3D:
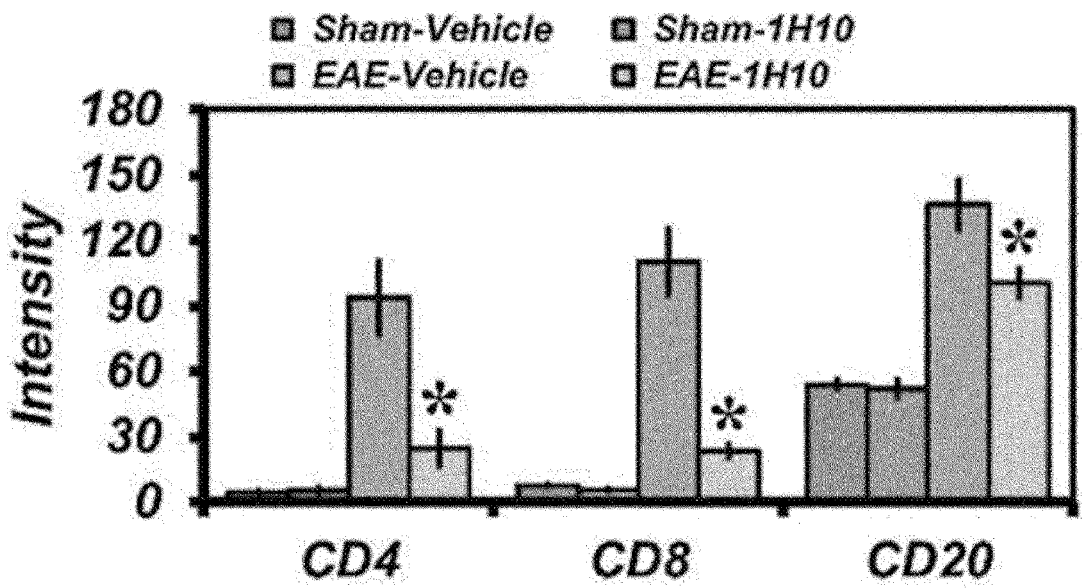
FIG. 3D is a graph representing the intensities of CD4, CD8, and CD20 immune responses in the thoracic spinal cords of sham-operated or EAE mice treated with 1H10 or only vehicle.
Figure 3E:
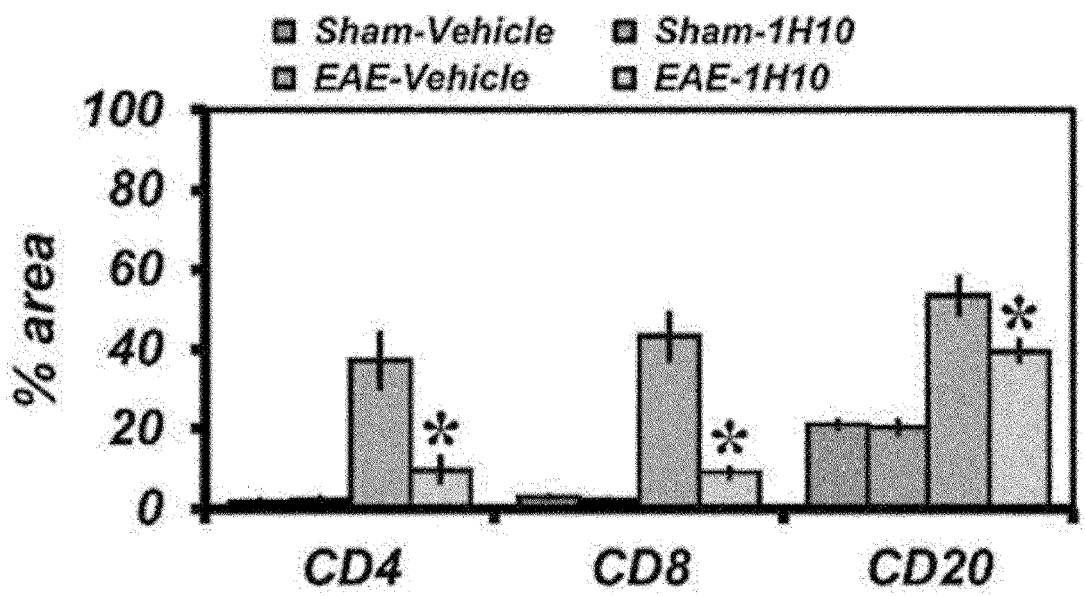
FIG. 3E is a graph representing the analysis of the percentage of CD4, CD8, and CD20-positive areas in the thoracic spinal cords of sham-operated or EAE mice treated with 1H10 or only vehicle.
Figure 3F:
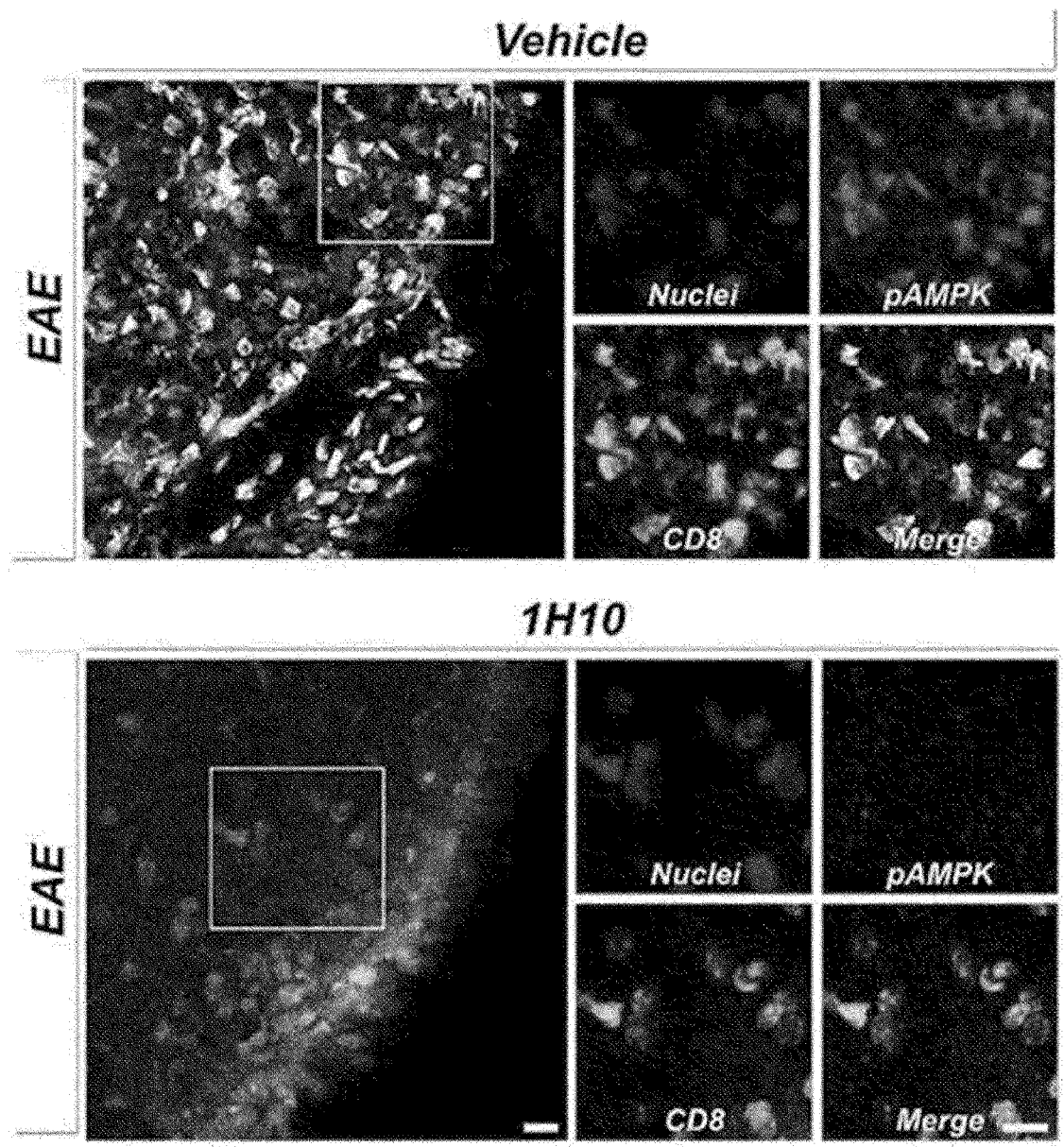
FIG. 3F is a series of representative immunofluorescence microscopic photographs showing CD8[+] T cells co-labeled with phospho-AMPKα 1/2 in the spinal cord from EAE mice treated with vehicle or 1H10.
Figure 3G:
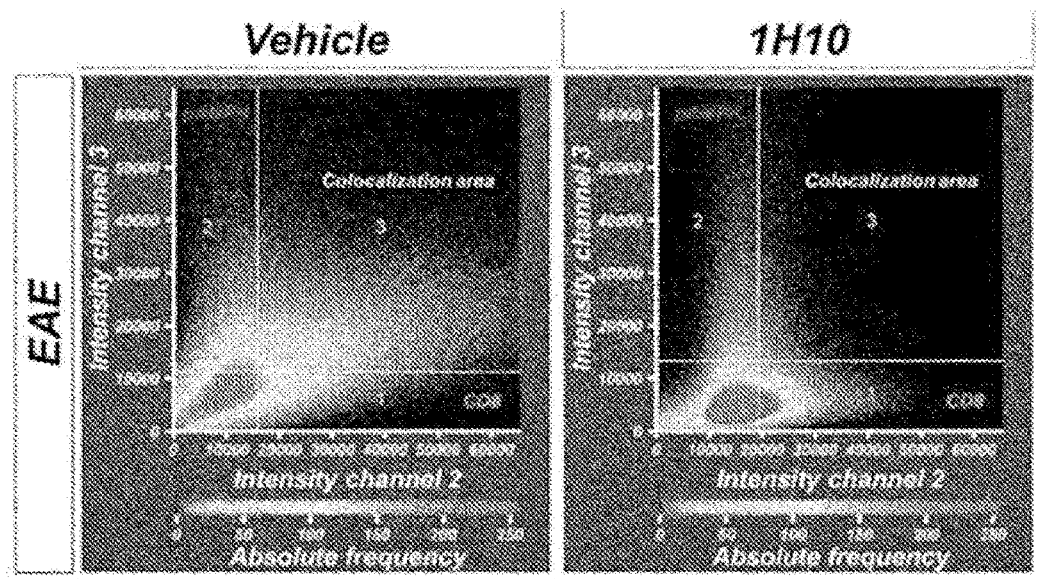
FIG. 3G is a graph representing the co-localization scattering plots of phospho-AMPKα 1/2 and CD8.
Figure 3H:
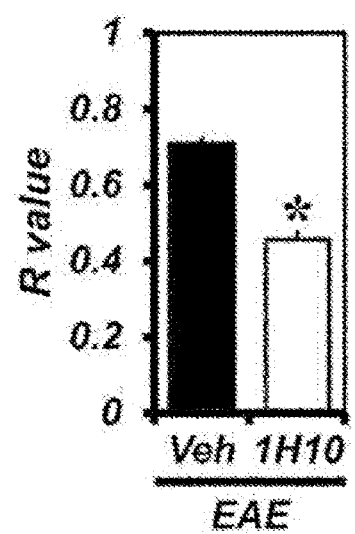
FIG. 3H is a graph representing the analysis of a quantitative co-localization parameter of CD8 and phospho-AMPKα 1/2 by measuring the Mander's overlap coefficient and Pearson's correlation coefficient (average±SEM; n=4) per group. **p<0.05.

As a result, it was confirmed that the mononuclear cell infiltration was significantly inhibited in the experimental group administered with 1H10, whereas a large number of mononuclear cells were distributed in the spinal cord white matter of the mice treated with vehicle only after EAE induction (FIGS. 3A and 3B). In addition, as a result of performing immunohistochemistry using anti-CD4, anti-CD8 and anti-CD20 antibodies to confirm the hypothesis that the mononuclear cells infiltrating into the spinal cord are immune cells, it was observed that the infiltration of the T and B cells was significantly inhibited in the experimental group administered with 1H10 while many CD4, CD8 and CD20+ cells after EAE induction while they were distributed around the spinal cord white matter in the experimental group administered with vehicle only (FIGS. 3C to 3E). In addition, according to a recent report, AMPK activity is known to enhance the survival of T cells. As a result of observing the activity of AMPK, phosphorylation of AMPK in CD8+ T cells infiltrated into the spinal cord after EAE induction was increased, but it was observed that it was significantly decreased in the experimental group administered with 1H10 (FIGS. 3F to 3H). The above results suggest that inhibition of AMPK by 1H10 of the present invention can alleviate the symptoms of EAE by reducing the survival of autoreactive T cells infiltrated into the spinal cord.

Experimental Example 5: Expression of Cytokines

Figure 19:
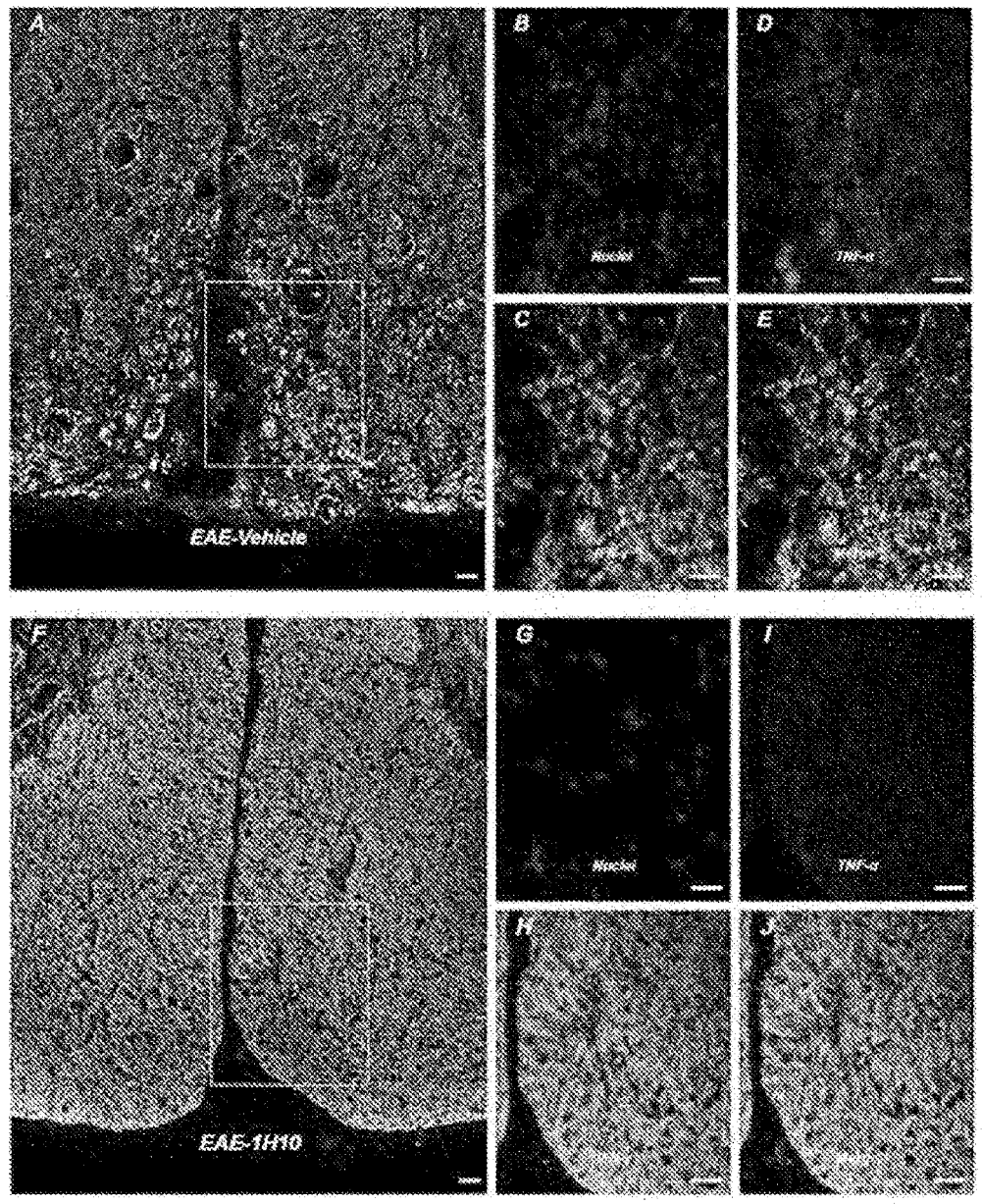
FIG. 19 shows the results of observations of the expression of IFN gamma and TNF alpha in the spinal cord of the EAE immunized mice treated with 1H10 (A to E) or vehicle only (F to J) on the 21$^{st}$ day after induction of EAE through double labeled confocal microscopic immunofluorescence imaging against interferon gamma (IFN-γ, green) (C, H) and tumor necrosis alpha (TNF-α, red) (D, I). Nuclei stained with DAPI (blue) (B, G). Scale bar, 20 μm.
Figure 20:
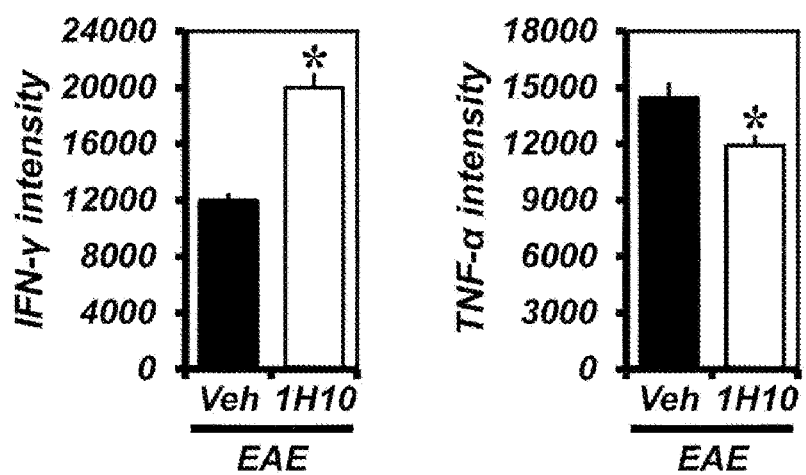
FIG. 20 is a graph representing the quantification of the immunofluorescence intensities of IFN gamma and TNF alpha in the spinal cord of EAE immunized mice treated with 1H10 or vehicle only on the 21$^{st}$ day after induction of EAE through immunofluorescence staining (mean±SEM; n=3-4 per group). *p<0.05 vs. EAE mice treated with vehicle only (Unpaired Student's t-test).

The present inventors investigated the expression of IFN gamma and TNF alpha among cytokines in the spinal cord of the mice on the 21$^{st}$ day after induction of EAE through immunofluorescence staining. As a result, it was observed that the expression of IFN gamma in the spinal cord white matter was increased in the experimental group administered with 1H10 after EAE induction compared to the group administered with vehicle only, whereas the expression of TNF alpha was decreased (FIGS. 19 and 20).

Experimental Example 6: Abnormal Accumulation of Zinc, Damage of BBB and Activity of MMP-9

The present inventors investigated EAE-induced abnormal accumulation of zinc in the spinal cord white matter, damage of blood-brain barrier (BBB) and activity of MMP-9 by administration of 1H10.

Figure 4A:
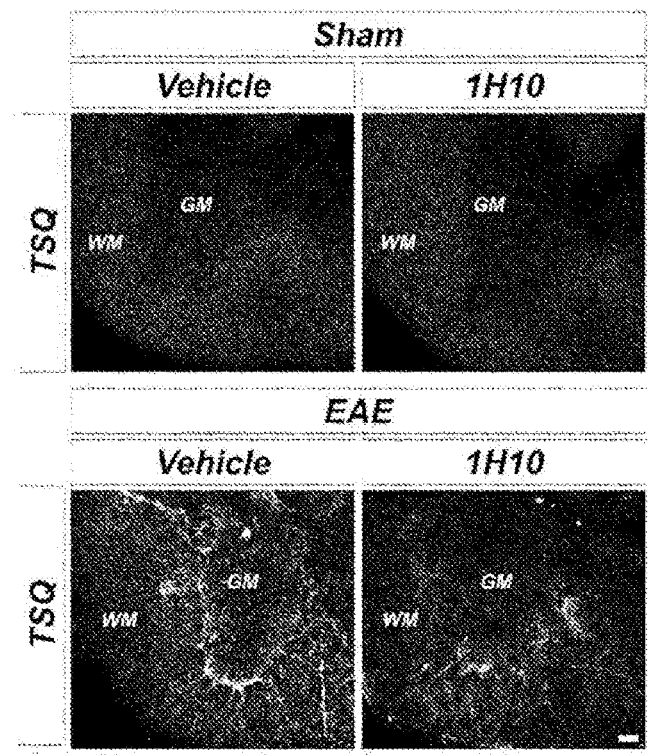
FIG. 4A is a series of microscopic photographs showing a portion of the spinal cord stained with TSQ to detect zinc accumulation. Scale bar, 100 μm.
Figure 4B:
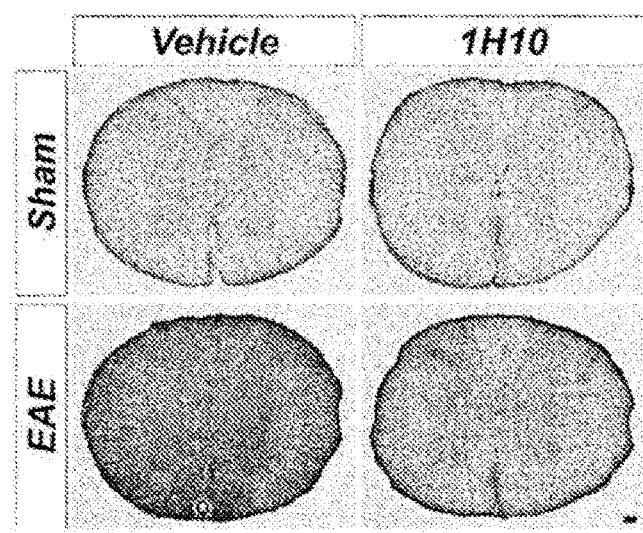
FIG. 4B is a series of microscopic photographs showing a portion of the spinal cord stained with anti-mouse immunoglobulin G (IgG) to detect endogenous IgG. Scale bar, 100 μm.
Figure 4C:
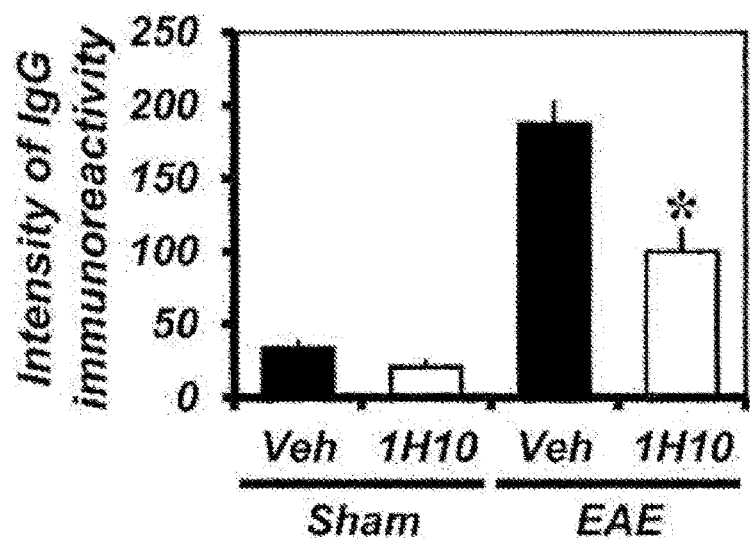
FIG. 4C is a graph representing the intensity of IgG leakage from the spinal cords in mice treated with vehicle or 1H10 at 3 weeks after initial immunization (mean±SEM; n=3-5 per group). **p<0.05.
Figure 4D:
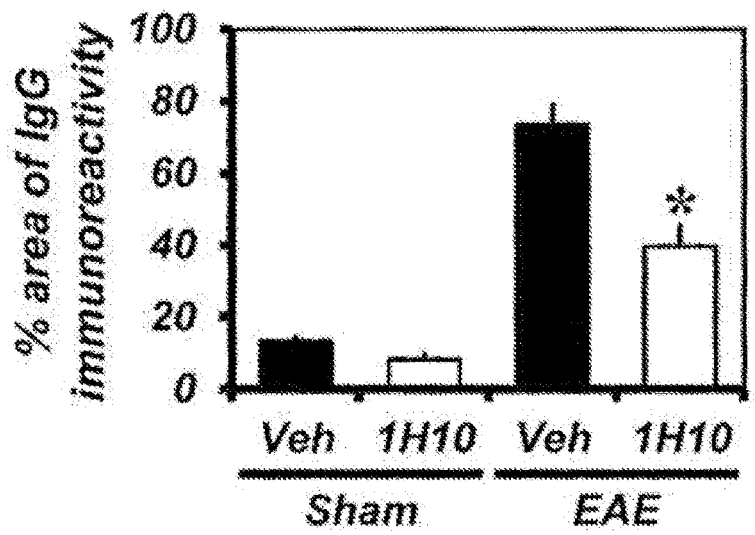
FIG. 4D is a graph representing the analysis the percentage of areas of IgG leakage from the spinal cords in mice treated with vehicle or 1H10 at 3 weeks after initial immunization (mean±SEM; n=3-5 per group). **p<0.05.
Figure 4E:
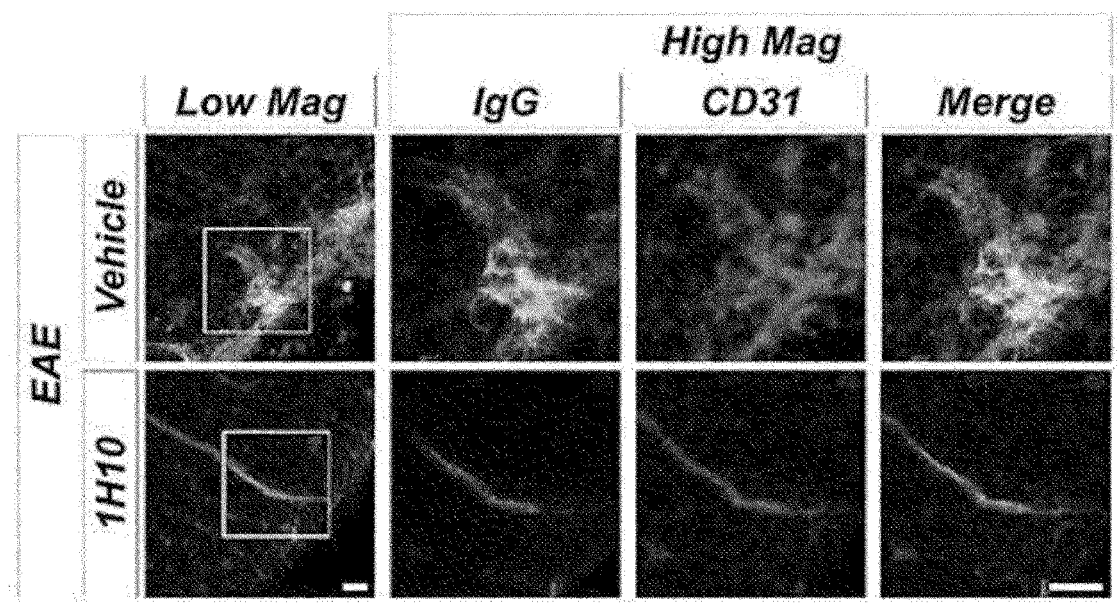
FIG. 4E is a series of double-labeled confocal microscopic images of CD31$^+$ endothelial cells (red) and endogenous mouse IgG molecules (green) in the white matter of the spinal cords from EAE mice not treated with 1H10. Scale bar, 20 μm.
Figure 4F:
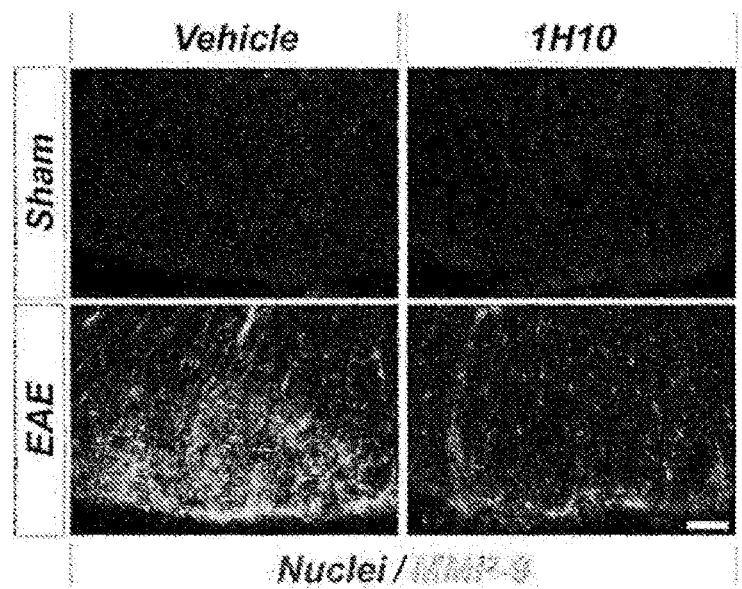
FIG. 4F is a series of immunofluorescence images showing the expression of MMP-9 in the white matter of the spinal cords. Scale bar, 50 μm.
Figure 4G:
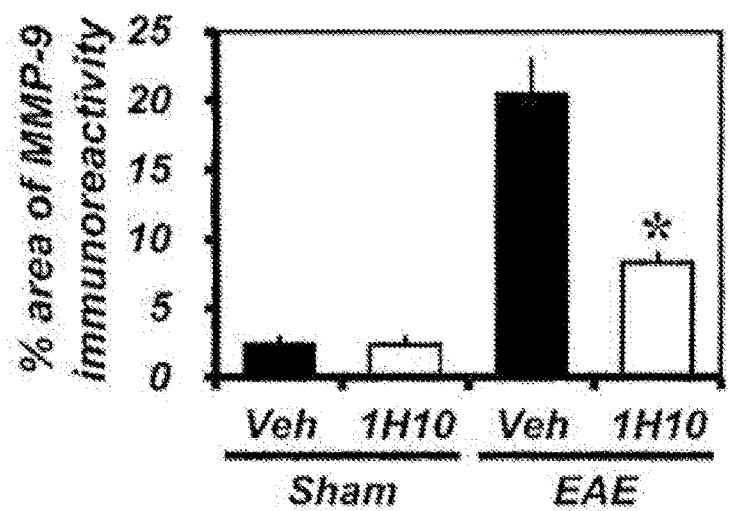
FIG. 4G is a graph showing the percentage of MMP-9 immunoreactivity area in the thoracic spinal cords of sham-operated and EAE mice treated with 1H10 or vehicle only, respectively. (mean±SEM; n=3-5 per group). **p<0.05.

As a result, no signal due to TSQ staining was observed in the white matter of normal tissues, but as a result of performing TSQ staining on the 21st day after EAE-induction, abnormal "patch like" fluorescence was observed in the white matter region of the spinal cord. The above pattern was not observed in the spinal cord of normal animals or vehicle-administered animals without EAE-induction, and it was confirmed that patch-like TSQ abnormal staining was significantly reduced by administration of 1H10 (FIGS. 4A and 4B). In addition, it has been reportet that after EAE-induction, the activity of MMP-9 is increased, and T-cells, B-cells, and other immune cells infiltrate into the central nervous system due to damage of BBB thereby and the infiltration of immune cells may destroy myelin sheath by disturbing immune system of central nerve system. Based on the previous researches, the present inventors conducted histological analysis of immunoglobulin G (IgG) leakage and measured MMP-9 activity to observe BBB damage. As a result, IgG staining due to damage of BBB was not detected in white matter or gray matter in either the mice administered with vehicle only or the mice administered with 1H10 (Sham group). However, in mice 3 weeks after MOG injection, IgG infiltration was significantly increased in both white matter and gray matter, and this phenomenon was significantly reduced by administration of 1H10 (FIGS. 4C to 4E). In addition, since the activity of MMP-9 is increased by zinc, it is thought that the observed increase of zinc in the white matter and the increase in the activity of MMP-9 are closely related to each other. It was confirmed that the activity of MMP-9 in the spinal cord white matter was inhibited in the experimental group administered with 1H10 compared to the control group administered with vehicle only (FIGS. 4F and 4G).

Experimental Example 7: Verification of Homeostasis Regulation of Zinc

Figure 5A:
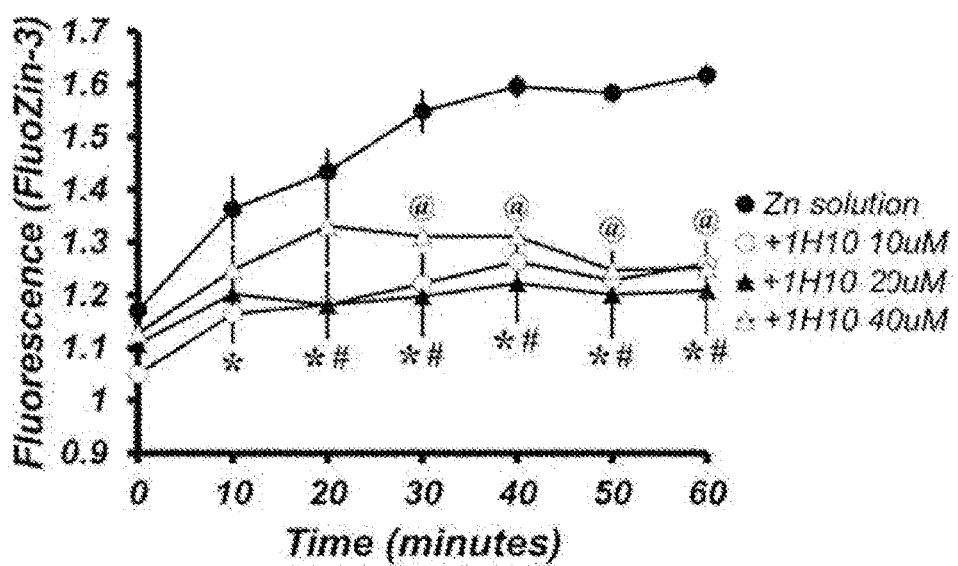
FIG. 5A is a graph representing an analysis of the distribution of FluoZin-3, a fluorescent indicator of zinc, in order to verity zinc homeostasis depending on the treatment of 1H10 according to an embodiment of the present invention.
Figure 5B:
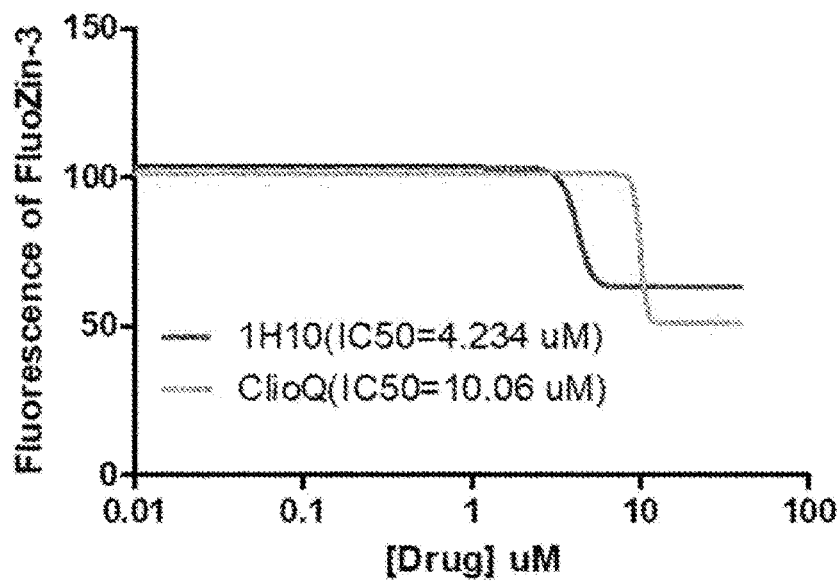
FIG. 5B is a graph representing an analysis of the distribution of FlipZom-3, a fluorescent indicator of zin in order to verify zinc homeostasis depending on the treatment of 1H10 according to an embodiment of the present invention.
Figure 6A:
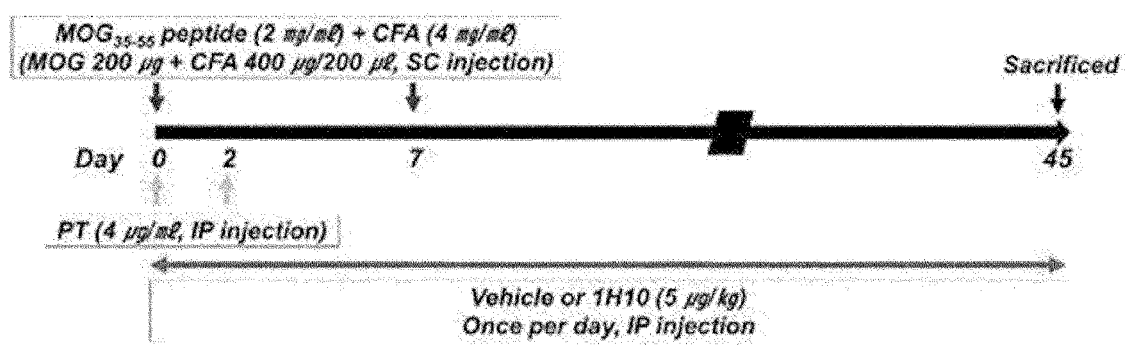
FIG. 6A is a timeline showing the experimental design for the analysis of long-term protection effect of 1H10 after induction of the EAE. After 1H10 was administered intraperitoneally once a day for the entire period, the mice were sacrificed 45 days after initial immunization.
Figure 6B:
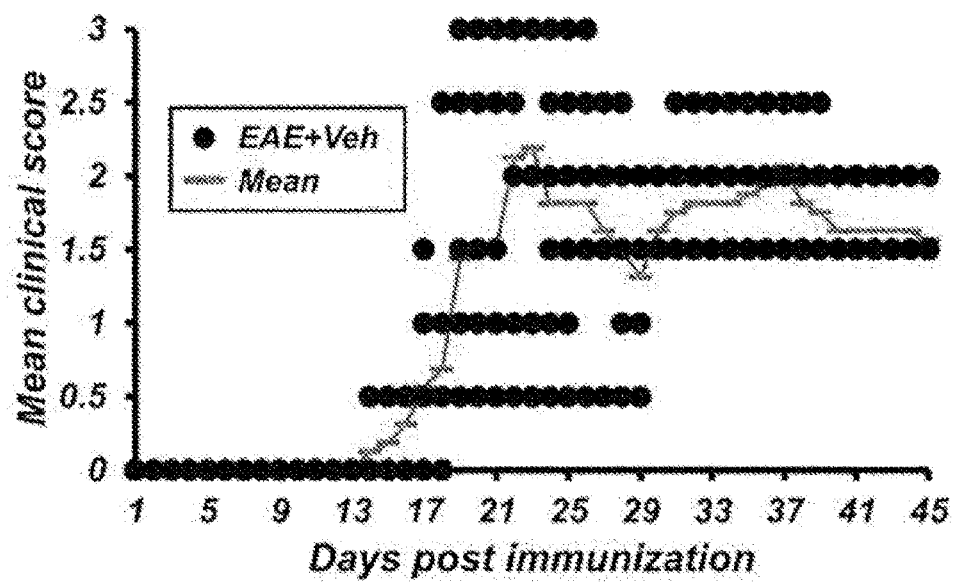
FIG. 6B is a graph representing clinical score of the EAE for the vehicle in order to analyze the long-term protection effect of 1H10 after induction of the EAE.
Figure 6C:
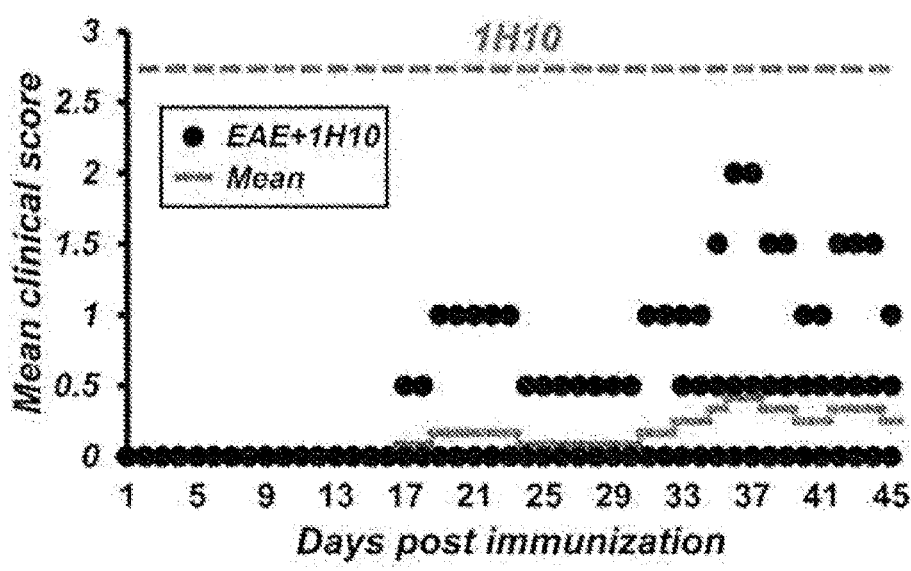
FIG. 6C is a graph representing clinical score of the EAE for 1H10 in order to analyze the long-term protection effect of 1H10 after induction of EAE.
Figure 6D:
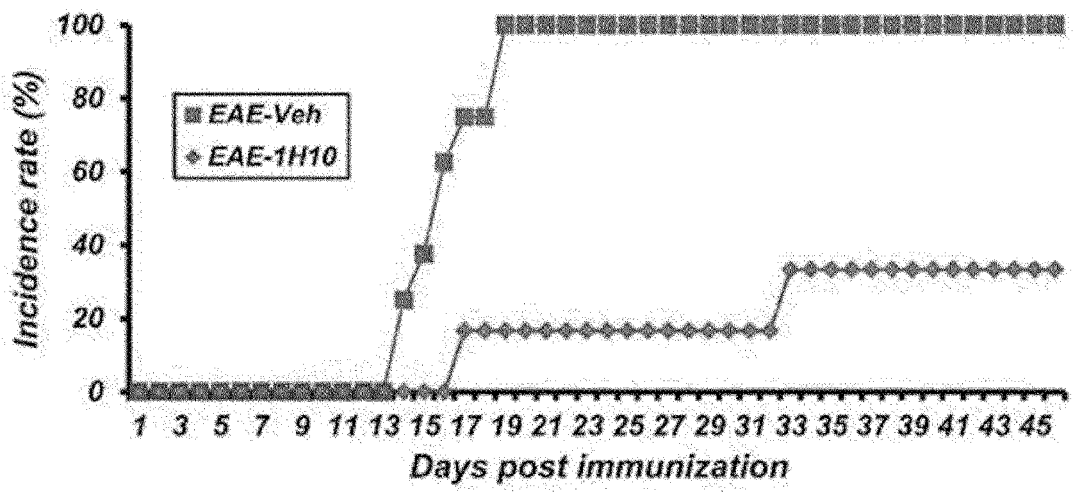
FIG. 6D is a graph representing disease incident rate (%) in the immunized mice treated with vehicle only or 1H10 in order to analyze the long-term protection effect of 1H10 after induction of EAE. The data are averaged±SEM (n=6-8 per group). **p<0.05.

As a result of verifying the possibility of zinc chelation according to 1H10 treatment using FluoZin-3, a material emitting fluorescence upon binding to free zinc, it was confirmed that the increase of intracellular zinc level was significantly reduced in experimental group administered with 1H10 (FIG. 5A). In addition, after reacting various concentrations of (0, 0.5, 1, 2, 5, 10, 20, 40 μM) 1H10 or clioquinol with 1 μM zinc and 5 μM fluorescent labeled drug for free zinc (FluoZin-3) in a test tube and fluorescence values were measured. The IC$_{50}$ values of each drug were determined as 4.234 μM and 10.06 μM, but the final FluoZin-3 fluorescence value was lower in clioquinol. 1H10 of the present invention binds zinc even at a lower concentration than clioquinol, but at a high concentration, zinc binding strength is considered to be lower than that of clioquinol (FIG. 5B). The above results suggest that 1H10 of the present invention can regulate zinc homeostasis in neurons by directly binding zinc as well as AMPK inhibitory activity Experimental Example 8: Long-Term Protective Effect After inducing EAE in mice, the present inventors administered 1H10 to the experimental animals intraperitoneally once a day for the entire period, and then sacrificing mice 45 days after initial immunization to investigate clinical symptoms and incidence rate (FIG. 6A). It was observed that clinical symptoms and the incidence rate were significantly reduced in the experimental group administered with 1H10 (FIGS. 6B to 6D). This proves that the administration of 1H10 is effective in relieving the symptoms of long-term EAE not only in the acute phase (21 days) but also in the chronic phase (45 days).

Experimental Example 9: Exploration of Similar Compounds and Investigation of Inhibitory Effect Against Zinc Toxicity According to an embodiment of the present invention, based on the structural similarity of 1H10 of the present invention, 25 similar compounds having a similar structure were purchased from a compound library manufacturer (InterBioScreen, Russia; Akos, Germany). Then, in order to induce zinc toxicity in the cortical neurons of the cultured mice, ZnCl$_2$ (400 μM) was treated for 10 minutes, and after 12.5 hours, the selected 25 compounds and the previously selected drug 1H10 were treated (20 μM) and it was determined whether cell death was inhibited through cell viability assay (Cell Counting Kit-8, Dojindo).

Figure 9:
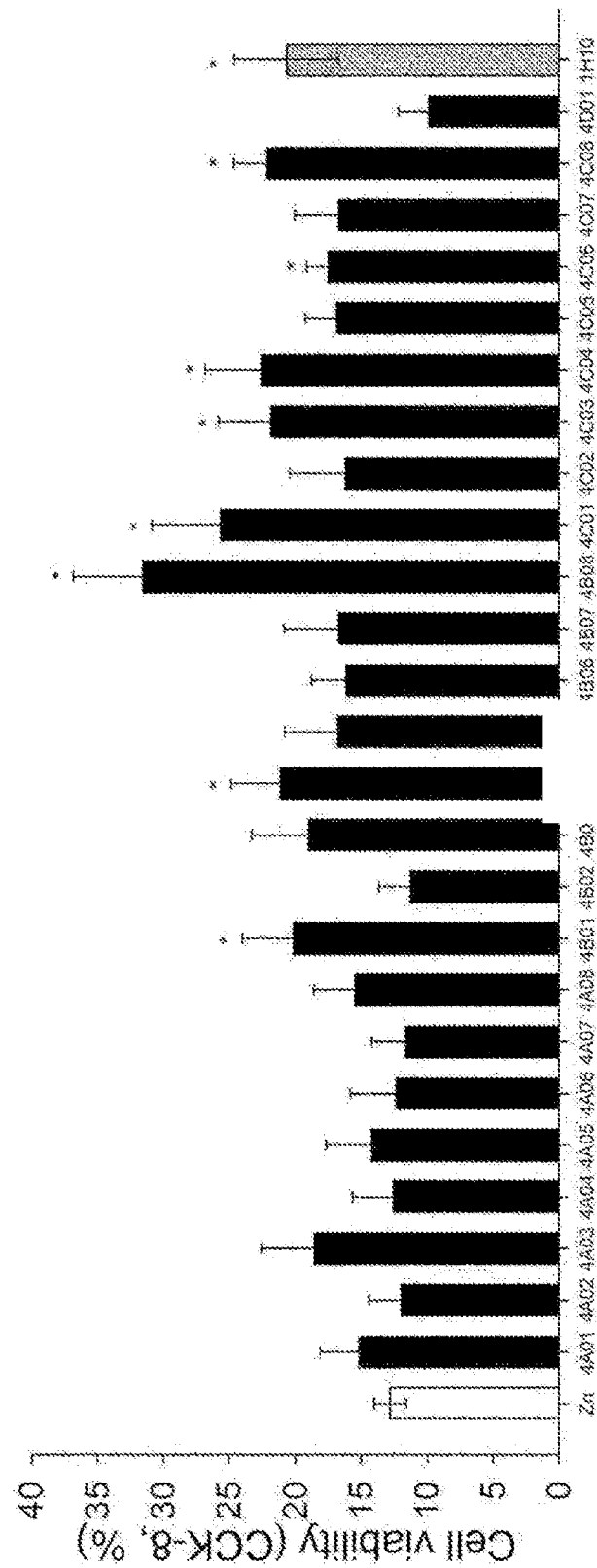
FIG. 9 is a graph representing an analysis of neural protection effects of 25 analog compounds having similar structures with 1H10 according to an embodiment of the present invention based on the structural analysis.

As a result, among the 25 new compounds treated above, 8 drugs (4B01, 4B04, 4B08, 4C01, 4C03, 4C04, 4C06, 4C08) showed a neuroprotective effect (FIG. 9). The names and structures of the 25 selected compounds are shown in Table 1 below.

TABLE 1

| Code Name | Structure | IUPAC Name |
|---|---|---|
| 4-A01 | 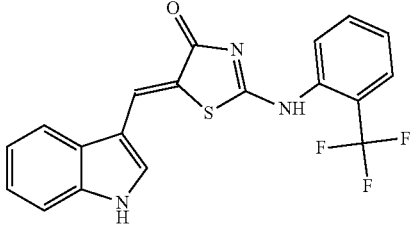 [SMILES: O=C1N=C(Nc2ccccc2C(F)(F)F)S/C1=C\c1c[nH]c2ccccc12] | (5Z)-5-(1H-Indol-3-ylmethylene)-2-{[2-(trifluoromethyl)phenyl]amino}-1,3-thiazol-4(5H)-one |
| 4-A02 | 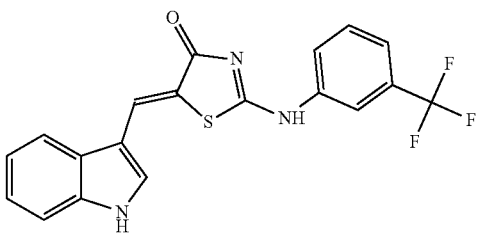 [SMILES: O=C1N=C(Nc2cccc(C(F)(F)F)c2)S/C1=C\c1c[nH]c2ccccc12] | (5Z)-5-(1H-Indol-3-ylmethylene)-2-{[3-(trifl(uoromethyl)phenyl]amino}-1,3-thiazol-4(5H)-one |
| 4-A03 | 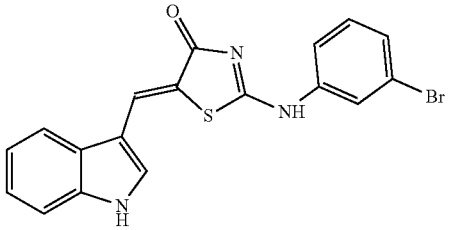 [SMILES: O=C1N=C(Nc2cccc(Br)c2)S/C1=C\c1c[nH]c2ccccc12] | (5Z)-2-[(3-Bromophenyl)amino]-5-(1H-indol-3-ylmethylene)-1,3-thiazol-4(5H)-one |
| 4-A04 | 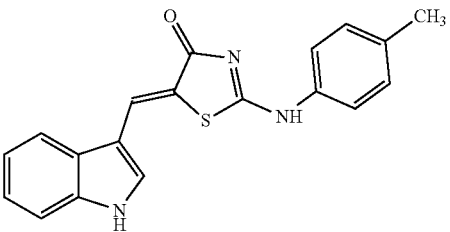 [SMILES: Cc1ccc(NC2=NC(=O)/C(=C/c3c[nH]c4ccccc34)S2)cc1] | (5Z)-5-(1H-Indol-3-ylmethylene)-2-[(4-methylphenyl)amino]-1,3-thiazol-4(5H)-one |
| 4-A05 | 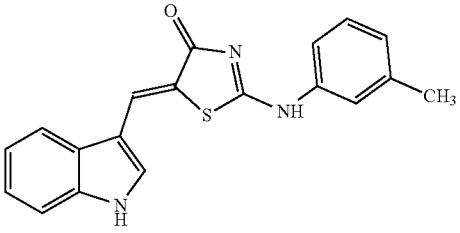 [SMILES: Cc1cccc(NC2=NC(=O)/C(=C/c3c[nH]c4ccccc34)S2)c1] | (5Z)-5-(1H-Indol-3-ylmethylene)-2-[(3-methylphenyl)amino]-1,3-thiazol-4(5H)-one |
| 4-A06 | 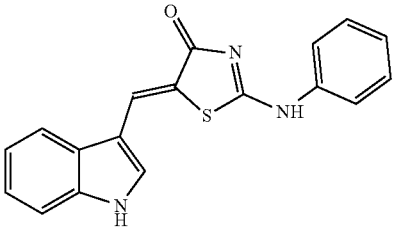 [SMILES: O=C1N=C(Nc2ccccc2)S/C1=C\c1c[nH]c2ccccc12] | (5Z)-2-Anilino-5-(1H-indol-3-ylmethylene)-1,3-thiazol-4(5H)-one |

TABLE 1-continued

| Code Name | Structure | IUPAC Name |
|---|---|---|
| 4-A07 | 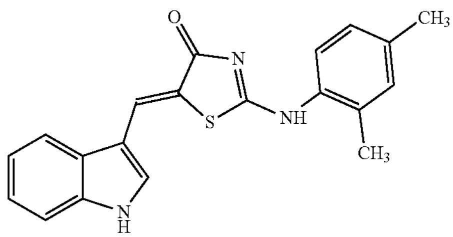 [SMILES: Cc1ccc(NC2=NC(=O)/C(=C/c3c[nH]c4ccccc34)S2)c(C)c1] | (5Z)-2-[(2,4-Dimethylphenyl)amino]-5-(1H-indol-3-ylmethylene)-1,3-thiazol-4(5H)-one |
| 4-A08 | 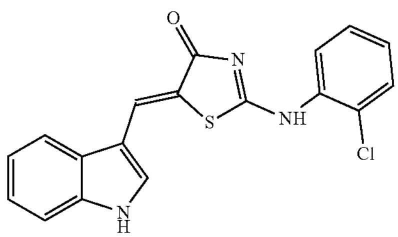 [SMILES: O=C1N=C(Nc2ccccc2Cl)S/C1=C\c1c[nH]c2ccccc12] | (5Z)-2-[(2-Chlorophenyl)amino]-5-(1H-indol-3-ylmethylene)-1,3-thiazol-4(5H)-one |
| 4-B01 | 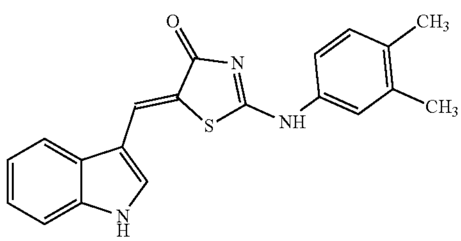 [SMILES: Cc1ccc(NC2=NC(=O)/C(=C/c3c[nH]c4ccccc34)S2)cc1C] | (5Z)-2-[(3,4-Dimethylphenyl)amino]-5-(1H-indol-3-ylmethylene)-1,3-thiazol-4(5H)-one |
| 4-B02 | 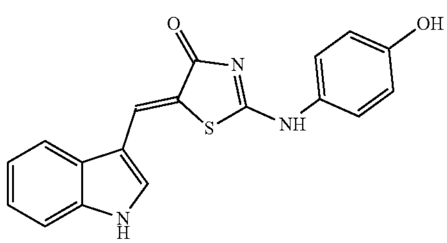 [SMILES: O=C1N=C(Nc2ccc(O)cc2)S/C1=C\c1c[nH]c2ccccc12] | (5Z)-2-[(4-Hydroxyphenyl)amino]-5-(1H-indol-3-ylmethylene)-1,3-thiazol-4(5H)-one |
| 4-B03 | 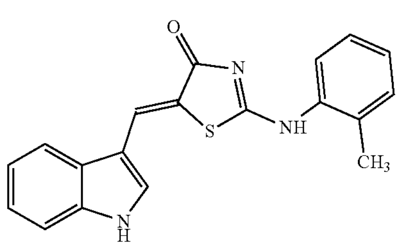 [SMILES: Cc1ccccc1NC1=NC(=O)/C(=C/c2c[nH]c3ccccc23)S1] | (5Z)-5-(1H-Indol-3-ylmethylene)-2-[(2-methylphenyl)amino]-1,3-thiazol-4(5H)-one |
| 4-B04 | 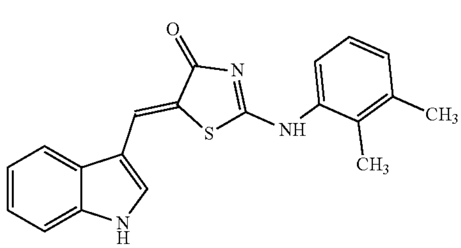 [SMILES: Cc1cccc(NC2=NC(=O)/C(=C/c3c[nH]c4ccccc34)S2)c1C] | (5Z)-2-[(2,3-Dimethylphenyl)amino]-5-(1H-indol-3-ylmethylene)-1,3-thiazol-4(5H)-one |

TABLE 1-continued

| Code Name | Structure | IUPAC Name |
| --- | --- | --- |
| 4-B05 | 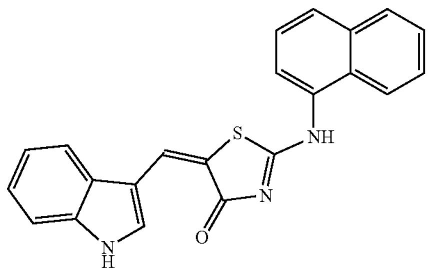 [SMILES: O=C1N=C(Nc2cccc3ccccc23)S/C1=C/c1c[nH]c2ccccc12] | (5E)-5-(1H-Indol-3-ylmethylene)-2-(1-naphthylamino)-1,3-thiazol-4(5H)-one |
| 4-B06 | 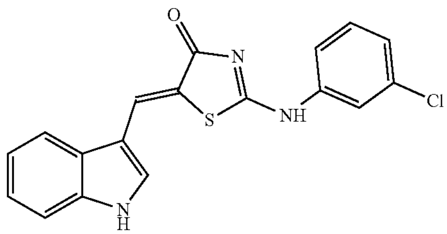 [SMILES: O=C1N=C(Nc2cccc(Cl)c2)S/C1=C\c1c[nH]c2ccccc12] | (5Z)-2-[(3-Chlorophenyl)amino]-5-(1H-indol-3-ylmethylene)-1,3-thiazol-4(5H)-one |
| 4-B07 | 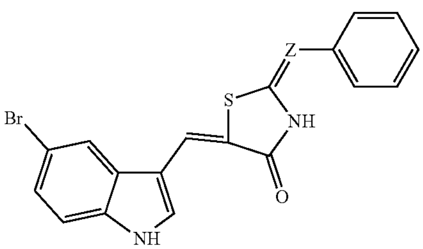 | (2E,5E)-5-((5-bromo-1H-indol-3-yl)methylene)-2-(phenylimino)thiazolidin-4-one |
| 4-B08 | 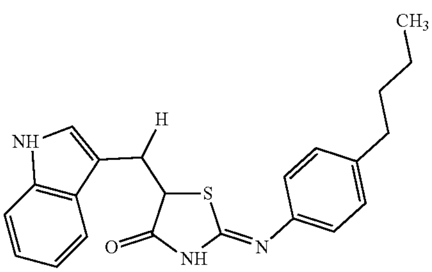 [SMILES: CCCCc1ccc(/N=C2/NC(=O)C(Cc3c[nH]c4ccccc34)S2)cc1] | (2Z,5E)-5-((1H-indol-3-yl)methylene)-2-((4-butylphenyl)imino)thiazolidin-4-one |
| 4-C01 | 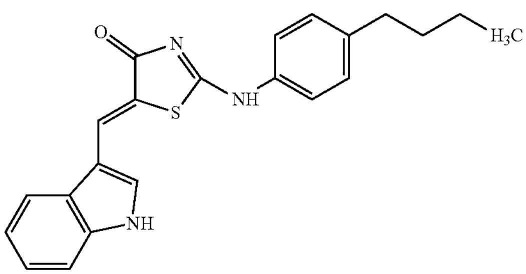 [SMILES: CCCCc1ccc(NC2=NC(=O)/C(=C/c3c[nH]c4ccccc34)S2)cc1] | (Z)-5-((1H-indol-3-yl)methylene)-2-((4-butylphenyl)amino)thiazol-4(5H)-one |
| 4-C02 | 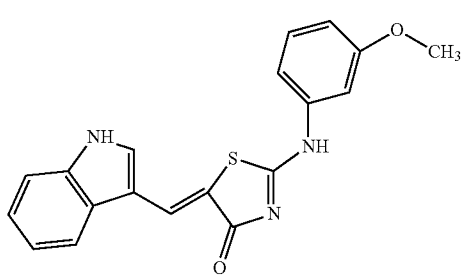 [SMILES: COc1cccc(NC2=NC(=O)/C(=C/c3c[nH]c4ccccc34)S2)c1] | (Z)-5-((1H-indol-3-yl)methylene)-2-((3-methoxyphenyl)amino)thiazol-4(5H)-one |

TABLE 1-continued

| Code Name | Structure | IUPAC Name |
|---|---|---|
| 4-C03 | 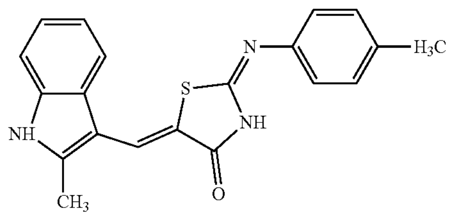 [SMILES: Cc1ccc(/N=C2\NC(=O)/C(=C/c3c(C)[nH]c4ccccc34)S2)cc1] | (2E,5Z)-5-((2-methyl-1H-indol-3-yl)methylene)-2-(p-tolylimino)thiazolidin-4-one |
| 4-C04 | 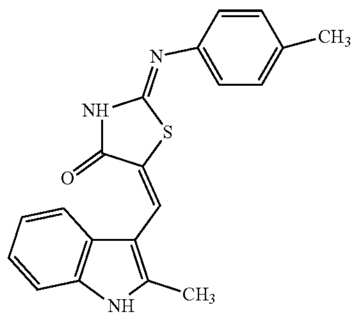 [SMILES: Cc1ccc(/N=C2/NC(=O)/C(=C\c3c(C)[nH]c4ccccc34)S2)cc1] | (2Z,5E)-5-((2-methyl-1H-indol-3-yl)methylene)-2-(p-tolylimino)thiazolidin-4-one |
| 4-C05 | 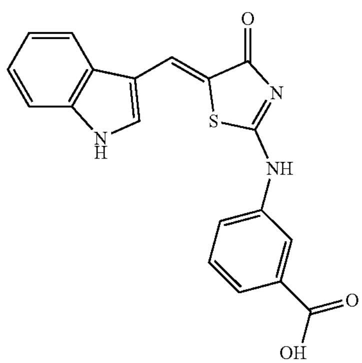 [SMILES: O=C1N=C(Nc2cccc(C(=O)O)c2)S/C1=C\c1c[nH]c2ccccc12] | (Z)-3-((5-((1H-indol-3-yl)methylene)-4-oxo-4,5-dihydrothiazol-2-yl)amino)benzoic acid |
| 4-C06 | 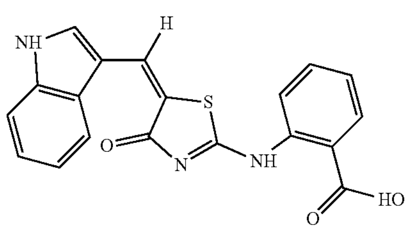 [SMILES: O=C1N=C(Nc2ccccc2C(=O)O)S/C1=C/c1c[nH]c2ccccc12] | (E)-2-((5-((1H-indol-3-yl)methylene)-4-oxo-4,5-dihydrothiazol-2-yl)amino)benzoic acid |
| 4-C07 | 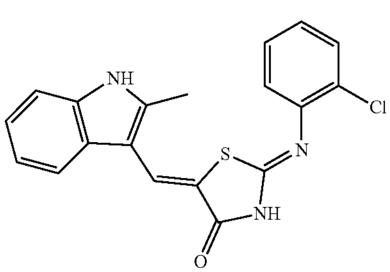 [SMILES: Cc1[nH]c2ccccc2c1/C=C1\S/C(=N\c2ccccc2Cl)NC1=O] | (2Z,5Z)-2-((2-chlorophenyl)imino)-5-((2-methyl-1H-indol-3-yl)methylene)thiazolidin-4-one |

TABLE 1-continued

| Code Name | Structure | IUPAC Name |
|---|---|---|
| 4-C08 | 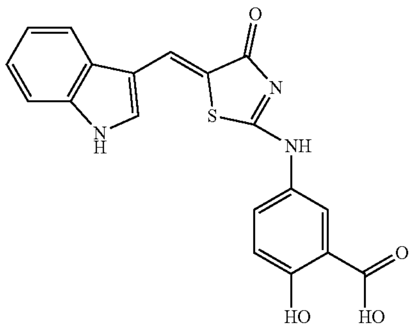 [SMILES: O=C1N=C(Nc2ccc(O)c(C(=O)O)c2)S/C1=C\c1c[nH]c2ccccc12] | (Z)-5-((5-((1H-indol-3-yl)methylene)-4-oxo-4,5-dihydrothiazol-2-yl)amino)-2-hydroxy benzoic acid |
| 4-D01 | 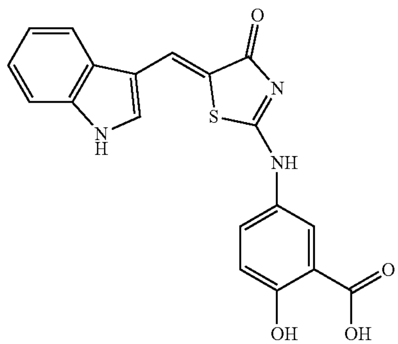 [SMILES: O=C1N=C(Nc2ccc(O)c(C(=O)O)c2)S/C1=C\c1c[nH]c2ccccc12] | (Z)-5-((1H-indol-3-yl)methylene)-N-(benzo[d][1,3]dioxol-5-yl)-4-methylene-4,5-dihydrothiazol-2-amine |

Experimental Example 10: Analysis of Oxidative Stress

The present inventors investigated the inhibitory effect against oxidative stress in addition to zinc toxicity for the eight drugs and 1H10 of the above examples. Specifically, oxidative damage induced neurotoxicity by treating mouse cortical neurons with $H_2O_2$ (100 μM) and $FeCl_2$ (100 μM) for about 4 hours and 20 hours, respectively, and treatment with the 8 selected drugs and 1H10 (20 μM). Thereafter, cytotoxicity was observed through LDH (Lactate Dehydrogenase) analysis.

Figure 10:
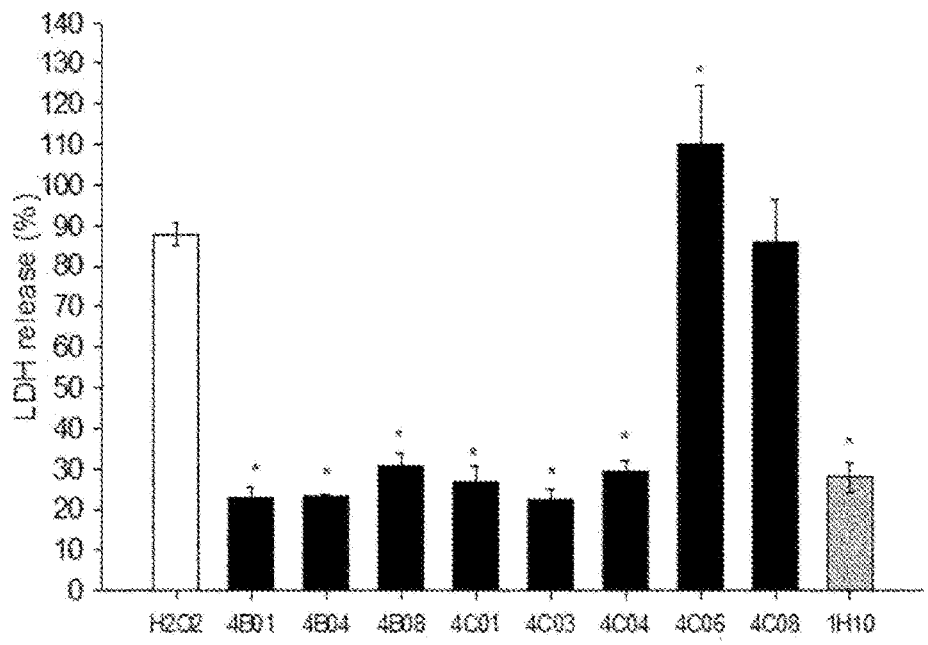
FIG. 10 is a graph representing an analysis of inhibitory effect against oxidative stress of the above-identified 25 novel compounds and 1H10 according to an embodiment of the present invention.
Figure 11:
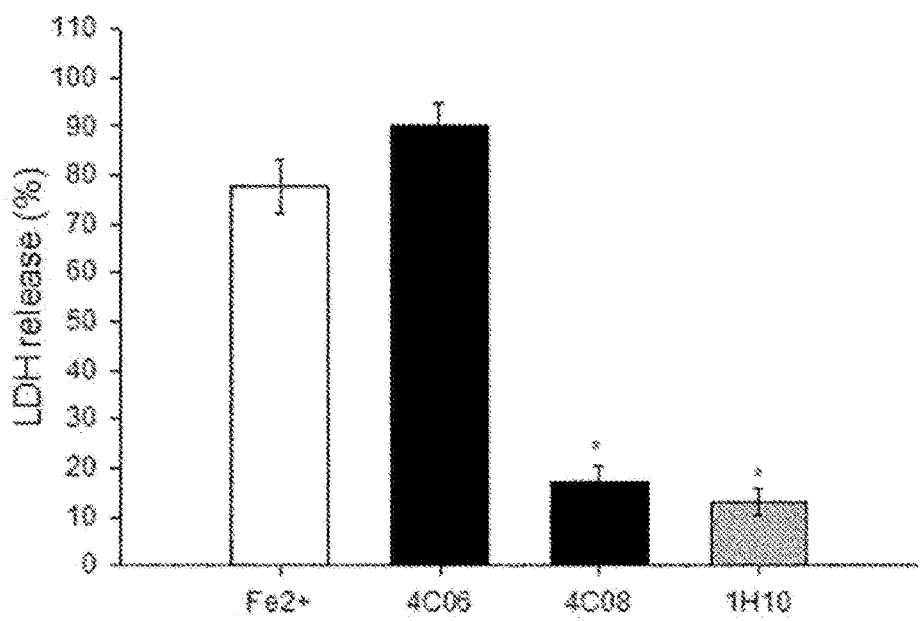
FIG. 11 is a graph representing an analysis of inhibitory effect against oxidative stress caused by treatment of eight novel compounds and 1H10 according to an embodiment of the present invention.

As a result, 6 drugs except 4C06 and 4C08 (4B01, 4B04, 4B08, 4C01, 4C03, 4C04) were found to significantly inhibit $H_2O_2$ toxicity (FIG. 10). In addition, as a result of confirming the oxidative damage caused by iron in addition to $H_2O_2$ for 4C06 and 4C08, it was found that the 4C08 inhibited the oxidative damage caused by iron (FIG. 11).

Experimental Example 11: Excitotoxicity Analysis

Figure 12:
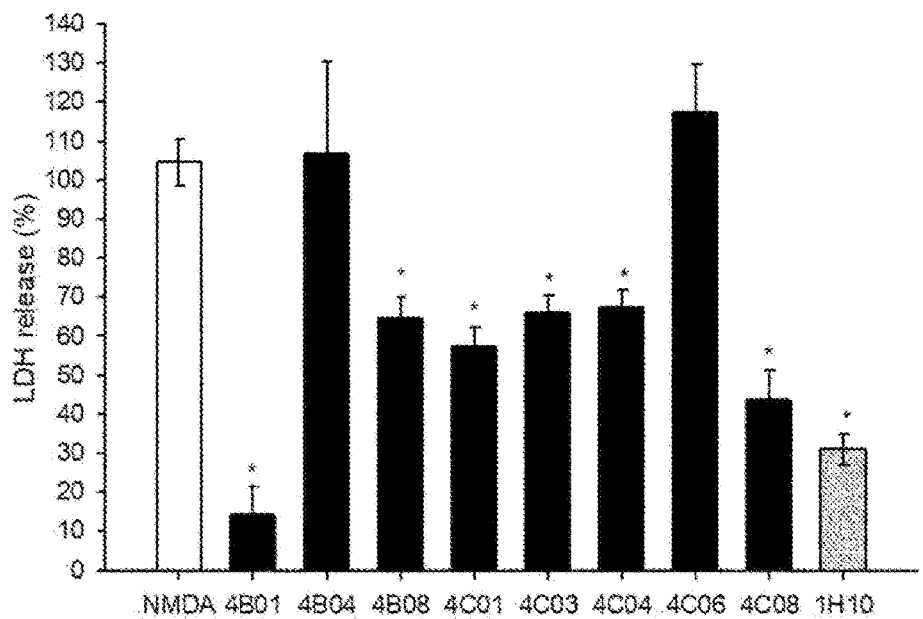
FIG. 12 is a graph representing an analysis of inhibitory effect against excitotoxicity by treating eight novel compounds and 1H10 according to an embodiment of the present invention.

The present inventors investigated the inhibitory effect against excitotoxicity of the eight drugs and 1H10 of the above examples. Specifically, excitotoxicity was induced by treatment with NMDA (N-methyl-D-aspartate, 50 μM) in mouse cortical neurons for 3 hours. As a result of observing excitotoxicity, 6 drugs (4B01, 4B08, 4C01, 4C03, 4C04, 4C08) except for 4B04 and 4C06 significantly inhibited the excitotoxicity caused by NMDA (FIG. 12).

Experimental Example 12: Apoptosis Analysis

Figure 13:
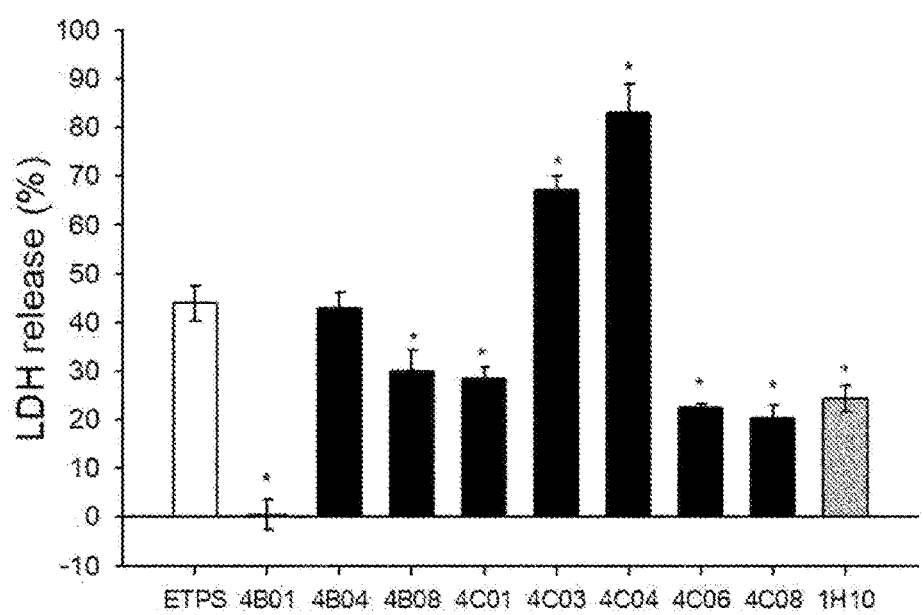
FIG. 13 is a graph representing an analysis of inhibitory effect against apoptosis by treating eight novel compounds and 1H10 according to an embodiment of the present invention.

The present inventors investigated the inhibitory effect against neuronal cell death of the eight drugs and 1H10 of the above examples. Specifically, neurotoxicity due to apoptosis was induced by treatment with etoposide (ETPS, 10 μM) in mouse cortical neurons for 20 hours. Then, the selected 8 drugs and 1H10 were treated (20 μM) and LDH cytotoxicity was observed. As a result, 5 drugs (4B01, 4B08, 4C01, 4C06, 4C08) except 4B04, 4C03, and 4C04 showed significant inhibitory effect against ETPS toxicity (FIG. 13).

Experimental Example 13: Zinc Binding Analysis

Figure 14:
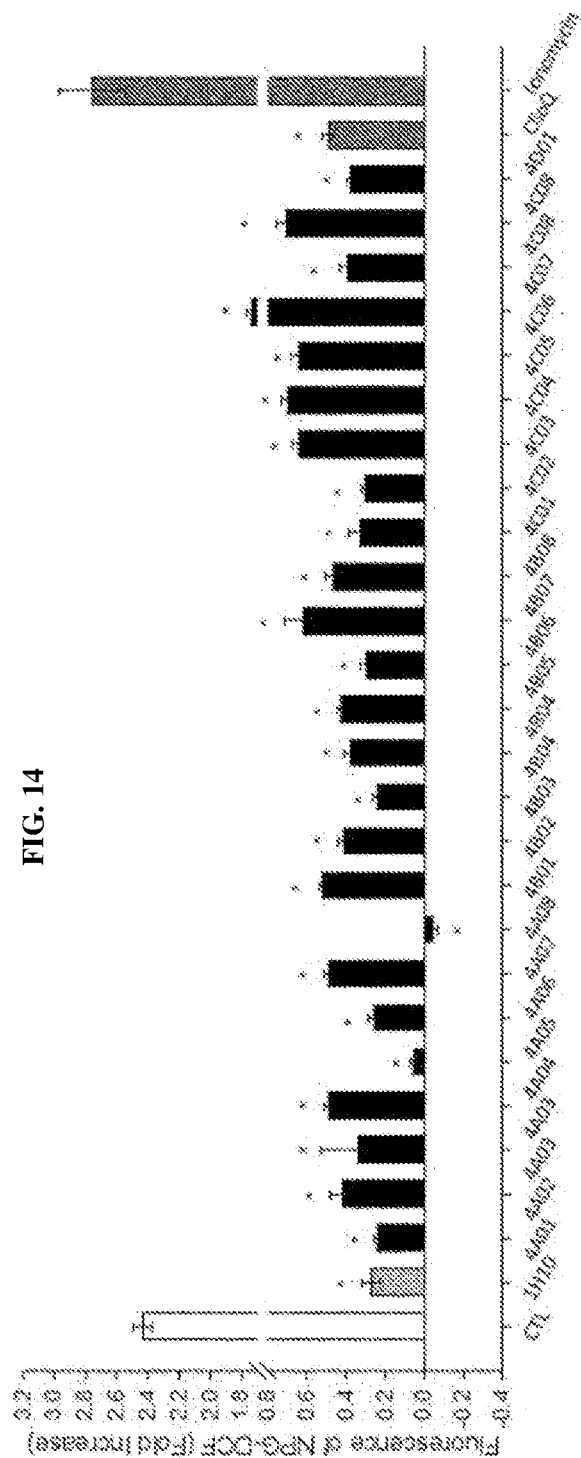
FIG. 14 is a graph representing results of zinc binding analysis of 25 new compounds and 1H10.

The present inventors performed a zinc binding assay for 25 compounds and 1H10 of the above examples. Specifically, degrees of free binding of the compounds to zinc were measured using zinc (20 μM) and a zinc fluorescent tracer, Newport green DCF (0.1 μM, Kd(Zn)=1 μM) together with 1H10 and 25 compounds (20 μM each) on a test tube. At this time, clioquinol, a zinc chelator, and ionomycin, a calcium ionophore, were used as controls (20 μM each). As a result, it was confirmed that all compounds except ionomycin were capable of binding to zinc (FIG. 14).

Experimental Example 14: AMPKα2 Inhibitory Activity

Figure 15:
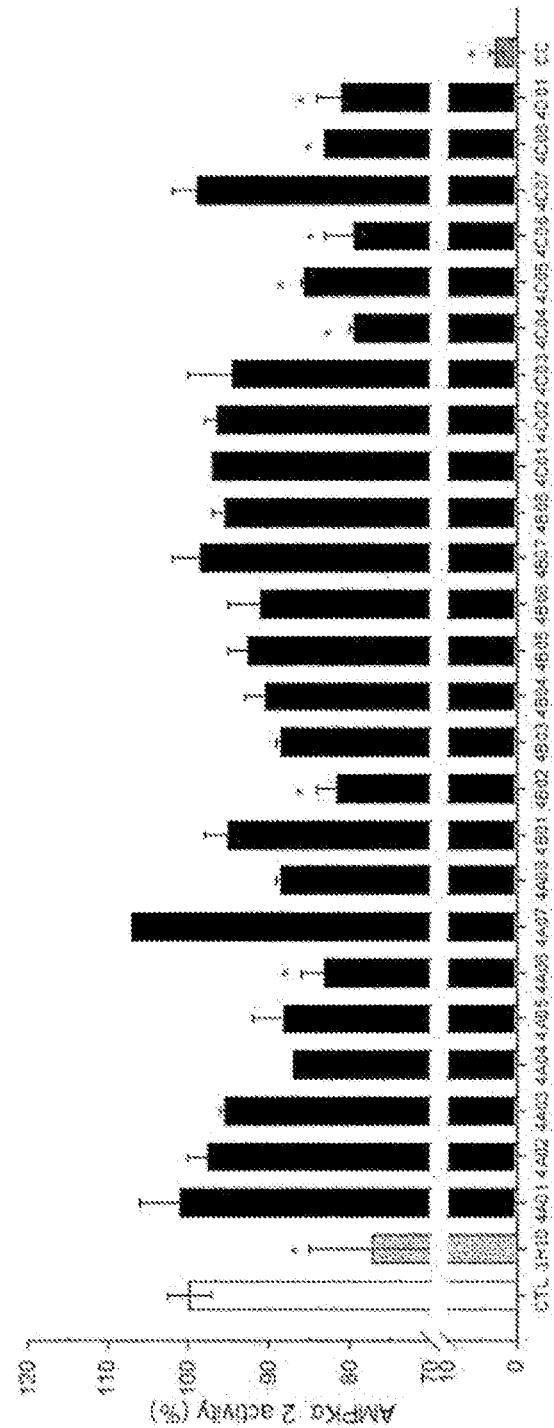
FIG. 15 is a graph representing an analysis AMPKα2 inhibition activity of 25 novel compounds and 1H10.

The present inventors measured the recombinant AMPKα2 enzymatic activity depending on the treatment of 1H10 and 25 compounds (10 μM, respectively), and the well-known AMPK inhibitor compound C (CC, 10 μM) through KinaseProfiler™ Service (Eurofins, UK). As a result, 4A06, 4B02, 4C04, 4C05, 4C06, 4C08, and 4D01 exhibited an AMPK inhibitory effect similar to that of 1H10 (FIG. 15).

Experimental Example 15: Intrinsic Toxicity Analysis

The present inventors performed intrinsic toxicity analysis for 4 drugs (4B01, 4B08, 4C01, 4C08) that showed a protective effect in common against all cytotoxicity (zinc toxicity, oxidative damage, excitotoxicity, apoptosis) and compared with that of 1H10. Specifically, 40 μM of each of the drugs was treated in a mouse cortical neuron culture, and LDH cytotoxicity was observed after 24 or 48 hours.

Figure 16:
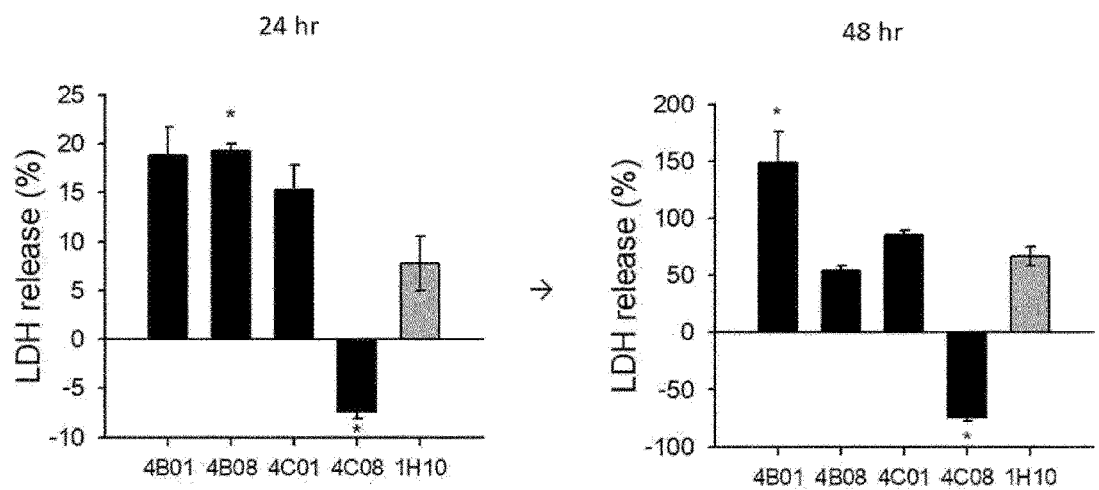
FIG. 16 is a graph representing results of toxicological analysis four new compounds and 1H10 conducted by the present inventors.

As a result, it was confirmed that 1H10 had intrinsic toxicity of 7.81±2.77% after 24 hours of drug treatment and 60.72±8.28% after 48 hours of drug treatment, but 4B01 had stronger intrinsic toxicity than 1H10 after 48 hours of drug treatment. In addition, 4B08 and 4C01 showed intrinsic toxicity with insignificant difference from 1H10, but 4C08 did not show intrinsic toxicity until 48 hours of drug treatment (FIG. 16).

In conclusion, the compounds according to an embodiment of the present invention have a protective effect on various toxic mechanisms such as excitotoxicity, oxidative stress, apoptosis, and zinc neurotoxicity related to conventional multiple sclerosis. In addition, it was demonstrated that by reducing MMP-9 activity through zinc chelation, it was possible to inhibit the occurrence of multiple sclerosis disease by preventing the infiltration and accumulation of immune cells in the spinal cord white matter, thereby reducing the autoimmune response. Therefore, 1H10 of the present invention can be used to develop drugs that can replace steroids and immunosuppressants, which have serious side effects due to long-term administration, and control the underlying problem.

Although the present invention has been described with reference to the above-described examples and experimental examples, these are merely exemplary, and those of ordinary skill in the art can will understand that it is possible to make various modifications and equivalent other examples and experimental examples therefrom. Therefore, the true scope of the present invention should be determined by the technical spirit of the appended claims.

What is claimed is:

1. A method for treating multiple sclerosis in a subject suffering from multiple sclerosis, comprising administering to the subject a therapeutically effective amount of (Z)-5-((1H-indol-3-yl)methylene)-2-((3-hydroxyphenyl)amino)thiazol-4(5H)-one.

2. A method for treating encephalomyelitis in a subject suffering from encephalomyelitis, comprising administering to the subject a therapeutically effective amount of (Z)-5-((1H-indol-3-yl)methylene)-2-((3-hydroxyphenyl)amino)thiazol-4(5H)-one.

* * * * *